(12) United States Patent
Ainsworth et al.

(10) Patent No.: US 8,328,846 B2
(45) Date of Patent: Dec. 11, 2012

(54) PROSTHETIC NUCLEUS WITH A PREFORMED MEMBRANE

(75) Inventors: Stephen D. Ainsworth, Wilmington, NC (US); Bradley J. Wessman, Wilmington, NC (US)

(73) Assignee: TranS1 Inc., Wilmington, NC (US)

( * ) Notice: Subject to any disclaimer, the term of this patent is extended or adjusted under 35 U.S.C. 154(b) by 401 days.

(21) Appl. No.: 12/648,758

(22) Filed: Dec. 29, 2009

(65) Prior Publication Data

US 2010/0137991 A1    Jun. 3, 2010

Related U.S. Application Data

(60) Division of application No. 12/061,556, filed on Apr. 2, 2008, now Pat. No. 8,088,147, which is a continuation-in-part of application No. 11/586,338, filed on Oct. 24, 2006, now Pat. No. 7,776,068.

(51) Int. Cl.
   *A61B 17/70* (2006.01)

(52) U.S. Cl. ....................................... 606/246

(58) Field of Classification Search .................. 606/246; 623/17.11–17.16
See application file for complete search history.

(56) References Cited

U.S. PATENT DOCUMENTS

| | | |
|---|---|---|
| 640,661 A | 1/1900 | Johnstone |
| 1,029,104 A | 6/1912 | Clark |
| 1,079,224 A | 11/1913 | Dodds |
| 1,086,144 A | 2/1914 | Dodds |
| 1,111,691 A | 9/1914 | Flannery |
| 2,586,556 A | 2/1952 | Mullikin |
| 3,272,541 A | 9/1966 | Latzen |
| 3,367,326 A | 2/1968 | Frazier |
| 3,837,347 A | 9/1974 | Tower |
| 4,175,555 A | 11/1979 | Herbert |
| 4,276,874 A | 7/1981 | Wolvek et al. |
| 4,297,047 A | 10/1981 | Farrant |
| 4,309,777 A | 1/1982 | Patil |
| 4,636,217 A | 1/1987 | Ogilvie et al. |
| 4,854,797 A | 8/1989 | Gourd |
| 4,858,601 A | 8/1989 | Glisson |
| 4,875,794 A | 10/1989 | Kern, Jr. |
| 4,932,925 A | 6/1990 | Roinestad et al. |
| 4,932,975 A | 6/1990 | Main et al. |

(Continued)

FOREIGN PATENT DOCUMENTS

WO    WO9100713 A1    1/1991

*Primary Examiner* — Nicholas Woodall

(74) *Attorney, Agent, or Firm* — Kevin E. Flynn; Flynn IP Law

(57) ABSTRACT

Multi-membrane prosthetic nucleus and implants using same are disclosed having an outermost membrane that is semi-compliant and limits the innermost membrane and any intermediate membranes that are highly compliant from bulging out of any opening in the annulus fibrosus. The outermost membrane may help protect the innermost membrane from trauma including any trauma before the innermost membrane is expanded through the injection of prosthetic nucleus material and trauma during the expansion of the innermost membrane in response to the injection of prosthetic nucleus material. Also disclosed is a coated membrane which combines the mechanical properties of the foundation layer with the low permeability to the passage of the flowable prosthetic material of the coating. This coated membrane is semi-compliant and prevents the prosthetic nucleus from bulging out of any openings in the annulus fibrosus. Use is made of injected prosthetic nucleus material that changes to a non-flowable state.

11 Claims, 33 Drawing Sheets

U.S. PATENT DOCUMENTS

| | | |
|---|---|---|
| 5,002,576 A | 3/1991 | Fuhrmann et al. |
| 5,059,193 A | 10/1991 | Kuslich |
| 5,061,137 A | 10/1991 | Gourd |
| 5,102,276 A | 4/1992 | Gourd |
| 5,108,430 A | 4/1992 | Ravo |
| 5,246,458 A | 9/1993 | Graham |
| 5,338,297 A | 8/1994 | Kocur et al. |
| 5,360,430 A | 11/1994 | Lin |
| 5,433,739 A | 7/1995 | Sluijter et al. |
| 5,480,401 A | 1/1996 | Navas |
| 5,562,737 A | 10/1996 | Graf |
| 5,702,453 A | 12/1997 | Rabbe et al. |
| 5,733,284 A | 3/1998 | Martin |
| 5,743,912 A | 4/1998 | Lehille et al. |
| 5,827,285 A | 10/1998 | Bramlet |
| 6,056,749 A | 5/2000 | Kuslich |
| 6,063,121 A | 5/2000 | Xavier et al. |
| 6,086,589 A | 7/2000 | Kuslich et al. |
| 6,093,205 A | 7/2000 | McLeod et al. |
| 6,124,007 A * | 9/2000 | Wang et al. .................. 428/35.2 |
| 6,187,048 B1 | 2/2001 | Milner et al. |
| 6,190,413 B1 | 2/2001 | Sutcliffe |
| 6,235,043 B1 | 5/2001 | Reiley et al. |
| 6,258,090 B1 | 7/2001 | Jackson |
| 6,428,576 B1 | 8/2002 | Haldimann |
| 6,440,168 B1 | 8/2002 | Cauthen |
| 6,506,194 B1 | 1/2003 | Hajianpour |
| 6,558,390 B2 | 5/2003 | Cragg |
| 6,582,466 B1 | 6/2003 | Gauchet |
| 6,582,468 B1 | 6/2003 | Gauchet |
| 6,626,943 B2 | 9/2003 | Eberlein et al. |
| 6,656,184 B1 | 12/2003 | White et al. |
| 6,682,561 B2 | 1/2004 | Songer et al. |
| 6,692,495 B1 | 2/2004 | Zacouto |
| 6,730,088 B2 | 5/2004 | Yeh |
| 6,733,532 B1 | 5/2004 | Gauchet et al. |
| 6,764,489 B2 | 7/2004 | Ferree |
| 6,821,277 B2 | 11/2004 | Teitelbaum |
| 6,899,716 B2 | 5/2005 | Cragg |
| 6,899,719 B2 | 5/2005 | Reiley et al. |
| 6,964,665 B2 | 11/2005 | Thomas et al. |
| 7,048,717 B1 | 5/2006 | Frassica |
| 7,077,865 B2 | 7/2006 | Bao et al. |
| 7,156,877 B2 | 1/2007 | Lotz et al. |
| 7,291,150 B2 | 11/2007 | Graf |
| 7,361,192 B2 | 4/2008 | Doty |
| 7,419,505 B2 | 9/2008 | Fleischmann et al. |
| 7,491,236 B2 | 2/2009 | Cragg et al. |
| 7,547,324 B2 | 6/2009 | Cragg et al. |
| 2001/0021852 A1 | 9/2001 | Chappius |
| 2002/0035400 A1 | 3/2002 | Bryan et al. |
| 2002/0068975 A1 | 6/2002 | Teitelbaum et al. |
| 2002/0198527 A1 | 12/2002 | Muckter |
| 2003/0028193 A1 | 2/2003 | Weil et al. |
| 2003/0055427 A1 | 3/2003 | Graf |
| 2003/0114930 A1 | 6/2003 | Lim et al. |
| 2003/0204261 A1 | 10/2003 | Eisermann et al. |
| 2004/0083002 A1 | 4/2004 | Belef et al. |
| 2004/0210227 A1 | 10/2004 | Trail et al. |
| 2004/0230309 A1 | 11/2004 | DiMauro et al. |
| 2005/0043796 A1 | 2/2005 | Grant et al. |
| 2005/0075711 A1 * | 4/2005 | Neary .......................... 623/1.11 |
| 2005/0113919 A1 | 5/2005 | Cragg et al. |
| 2005/0113928 A1 * | 5/2005 | Cragg et al. ............... 623/17.16 |
| 2005/0113929 A1 | 5/2005 | Cragg et al. |
| 2005/0149191 A1 | 7/2005 | Cragg et al. |
| 2005/0177167 A1 | 8/2005 | Muckter |
| 2005/0277940 A1 | 12/2005 | Neff |
| 2006/0084983 A1 | 4/2006 | Kim |
| 2006/0085073 A1 | 4/2006 | Raiszadeh |
| 2006/0229609 A1 | 10/2006 | Wang |
| 2007/0168042 A1 | 7/2007 | Hudgins et al. |
| 2007/0282443 A1 | 12/2007 | Globerman et al. |

* cited by examiner

| FIG. 6A |
|---|
| FIG. 6B |
| FIG. 6C |

FIG. 6B

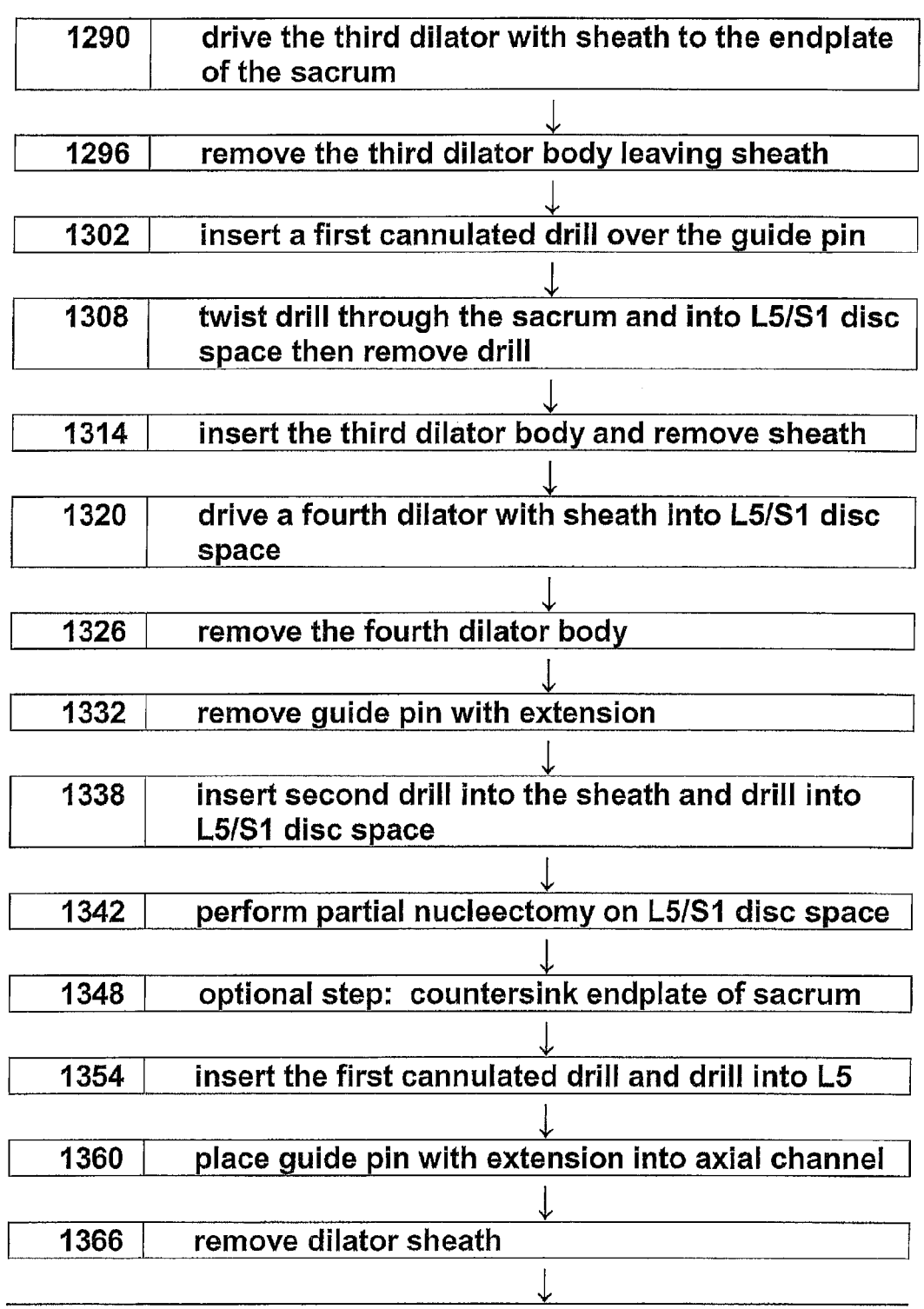

| 1290 | drive the third dilator with sheath to the endplate of the sacrum |
| 1296 | remove the third dilator body leaving sheath |
| 1302 | insert a first cannulated drill over the guide pin |
| 1308 | twist drill through the sacrum and into L5/S1 disc space then remove drill |
| 1314 | insert the third dilator body and remove sheath |
| 1320 | drive a fourth dilator with sheath into L5/S1 disc space |
| 1326 | remove the fourth dilator body |
| 1332 | remove guide pin with extension |
| 1338 | insert second drill into the sheath and drill into L5/S1 disc space |
| 1342 | perform partial nucleectomy on L5/S1 disc space |
| 1348 | optional step: countersink endplate of sacrum |
| 1354 | insert the first cannulated drill and drill into L5 |
| 1360 | place guide pin with extension into axial channel |
| 1366 | remove dilator sheath |

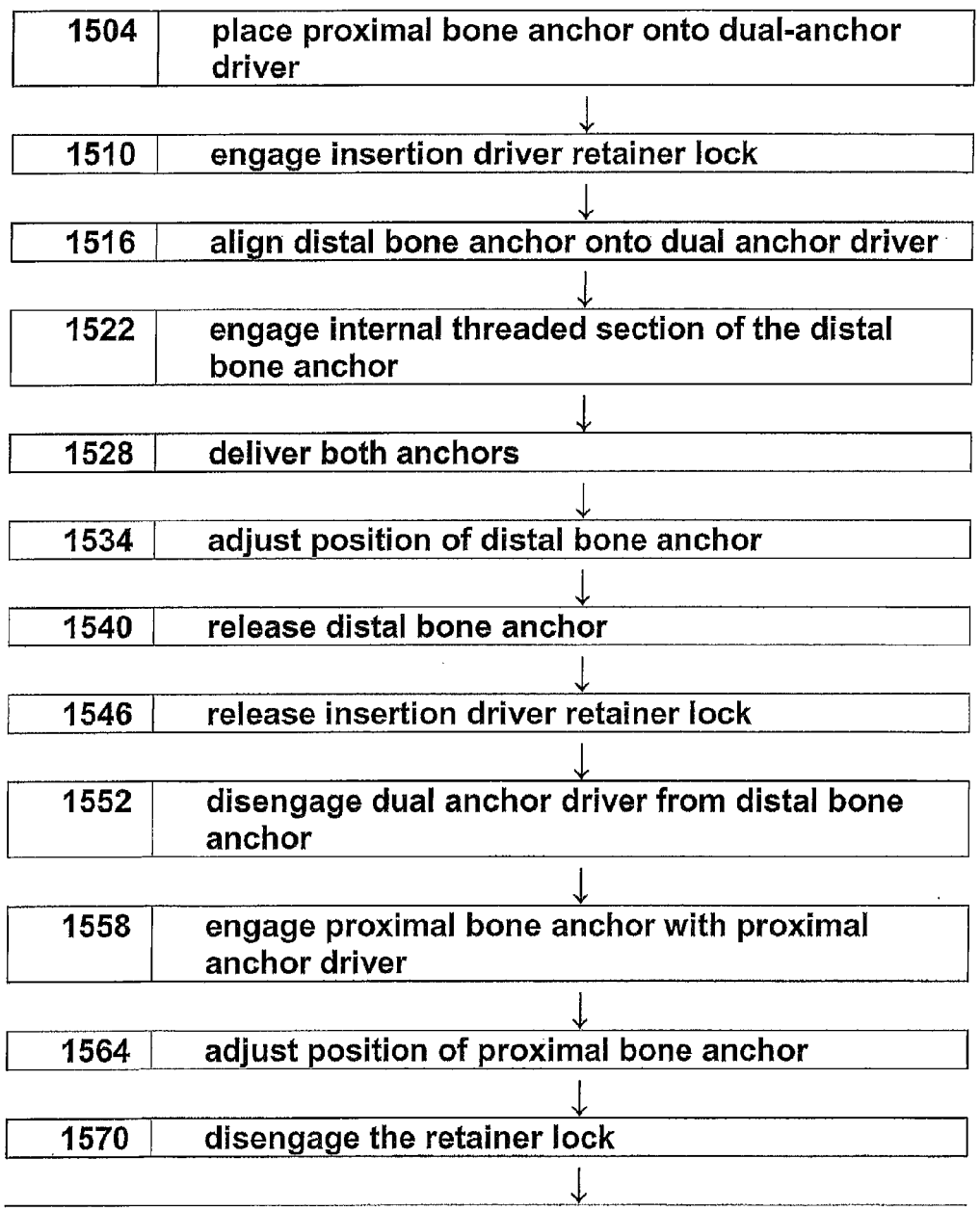

PROSTHETIC NUCLEUS WITH A PREFORMED MEMBRANE

This application claims priority to and incorporates by reference co-pending and commonly assigned U.S. patent application Ser. No. 11/586,338 for Spinal Motion Preservation Assemblies and U.S. patent application Ser. No. 12/061,556 for Multi-Membrane Prosthetic Nucleus.

This application incorporates by reference a set of United States applications, including: U.S. patent application Ser. No. 11/712,548 for Cutter for Preparing Intervertebral Disc Space, U.S. patent application Ser. No. 10/971,779 for Access Instrumentation Systems, and U.S. patent application Ser. No. 11/501,351 for Exchange System for Axial Spinal Procedures. This application incorporates by reference U.S. Pat. No. 6,558,390 for Methods and Apparatus for Performing Therapeutic Procedures in the Spine.

While these five applications and a patent have been incorporated by reference to provide additional detail it should be noted that these other applications were written at an earlier time and had a different focus from the present application. Thus, to the extent that the teachings or use of terminology differ in any of these incorporated applications from the present application, the present application controls.

BACKGROUND

Field of the Disclosure

This disclosure relates generally to implantable device assemblies, instrumentation systems, and methods for accessing and treating a spinal motion segment via various access routes including a minimally-invasive trans-sacral approach (as described in U.S. Pat. No. 6,558,390 which is incorporated by reference above) and procedures for the deployment of implantable components and assemblies some with components that are anchored in bone. Collectively the various implantable components and assemblies can be used to distract, decompress, and stabilize a motion segment while preserving motion in vertebral motion segments in the human spine to relieve lower back pain, restore physiological function of the lumbar spine, and prevent progression or transition of degenerative disease. More specifically, the present disclosure generally relates to spinal motion preservation assemblies (MPA) including assemblies adapted to be introduced percutaneously through tissue to an access point on the spine in a minimally invasive, low trauma manner, to provide therapy to the spine.

Although trans-sacral delivery methods are discussed at length, selected teachings of the present disclosure are applicable to other delivery routes including traditional lateral access to the intervertebral disc space and the relevant motion segment.

Overview

The present disclosure is an extension of work in a series of patent applications (some now issued patents) with a common assignee. Much of the work is described in great detail in the many applications referenced above and incorporated by reference into this application. Accordingly, the background of the disclosure provided here does not repeat all of the detail provided in the earlier applications, but instead highlights how the present disclosure adds to this body of work.

Introduction to Relevant Anatomy and Terms

The spinal column is a complex system of bone segments (vertebral bodies and other bone segments) which are in most cases separated from one another by discs in the intervertebral disc spaces (sacral vertebrae are an exception). The vertebrae of the spinal cord are conventionally subdivided into several sections. Moving from the head to the tailbone, the sections are cervical, thoracic, lumbar, sacral, and coccygeal. The individual vertebral bodies within the sections are identified by number starting at the vertebral body closest to the head. The trans-sacral approach is well suited for access to vertebral bodies in the lumbar section and the sacral section. As the various vertebral bodies in the sacral section are usually fused together in adults, it is sufficient and perhaps more descriptive to merely refer to the sacrum rather than the individual sacral components.

In the context of the present disclosure, a "motion segment" includes adjacent vertebrae, that is, an inferior and a superior vertebral body, and the intervertebral disc space separating said two vertebral bodies, whether denucleated space or with intact or damaged spinal discs. Unless previously fused, each motion segment contributes to the overall ability of the spine to flex to provide support for the movement of the trunk and head.

With respect to motion, vertebrae move relative to one other in order to allow the spine to bend forward (flexion), bend backward (extension), bend to the right or left (lateral bending), twist (rotate in the z-axis) and other forms of movement.

The individual motion segments within the spinal columns allow movement within constrained limits and provide protection for the spinal cord. The discs are important to cushion and distribute the large forces that pass through the spinal column as a person walks, bends, lifts, or otherwise moves. Unfortunately, for a number of reasons referenced below, for some people, one or more discs in the spinal column will not operate as intended. The reasons for disc problems range from a congenital defect, disease, injury, or degeneration attributable to aging. Often when the discs are not operating properly, the gap between adjacent vertebral bodies is reduced and this causes additional problems including pain.

The nucleus pulposus that forms the center portion of the intervertebral disc consists of 80% water that is absorbed by the proteoglycans in a healthy adult spine. With aging, the nucleus becomes less fluid and more viscous and sometimes even dehydrates and contracts (sometimes referred to as "isolated disc resorption") causing severe pain in many instances. The spinal discs serve as "dampeners" between each vertebral body that minimize the impact of movement on the spinal column, and disc degeneration, marked by a decrease in water content within the nucleus, renders discs less effective in transferring loads to the annulus layers. In addition, the annulus tends to thicken, desiccate, and become more rigid, lessening its ability to elastically deform under load and making it susceptible to fracturing or fissuring, and one form of degeneration of the disc thus occurs when the annulus fissures or is torn. The fissure may or may not be accompanied by extrusion of nucleus material into and beyond the annulus fibrosus. The fissure itself may be the sole morphological change, above and beyond generalized degenerative changes in the connective tissue of the disc, and disc fissures can nevertheless be painful and debilitating. Biochemicals contained within the nucleus are enabled to escape through the fissure and irritate nearby structures.

A fissure also may be associated with a herniation or rupture of the annulus causing the nucleus to bulge outward or extrude out through the fissure and impinge upon the spinal column or nerves (a "ruptured" or "slipped" disc). With a contained disc herniation, the nucleus may work its way partly through the annulus but is still contained within the annulus or beneath the posterior longitudinal ligament, and there are no free nucleus fragments in the spinal canal. Nevertheless, even a contained disc herniation is problematic because the outward protrusion can press on the spinal cord or on spinal nerves causing sciatica.

A range of therapies have been developed to alleviate the pain associated with disc problems. One class of solutions is to remove the failed disc and then fuse the two adjacent vertebral bodies together with a permanent but inflexible spacing, also referred to as static stabilization. Fusing one section together ends the ability to flex in that motion segment. While the loss of the normal physiologic disc function for a motion segment through fusion of a motion segment may be better than continuing to suffer from the pain, it would be better to alleviate the pain and yet retain all or much of the normal performance of a healthy motion segment.

Another class of therapies attempts to repair the disc so that it resumes operation with the intended intervertebral spacing and mechanical properties. One type of repair is the replacement of the original damaged disc with a prosthetic material. This type of therapy is called by different names such as dynamic stabilization or spinal motion preservation.

Within the category of spinal motion preservation procedures there are sub-types. For patients with severe problems, a total disc replacement (TDR) may be appropriate. In a total disc replacement, the entire disc (nucleus, annulus fibrosus, and adjacent vertebral endplates) are removed. This is a major modification to the motion segment.

Another category of therapy is a prosthetic nucleus replacement which could be done in some situations percutaneously. This category of therapy is suitable for patients with less severe problems. The present disclosure may be used to provide a prosthetic nucleus that falls into this category. A prosthetic nucleus implant of this type works in conjunction with the patient's annulus fibrosus.

A third category of therapy is percutaneous disc replacement (PDR) which like the TDR may be used when the patient's nucleus fibrosus is seriously degraded or compromised. Thus, PDR may be used in a progressive series of therapy for some patients that have seriously compromised annulus fibrosus even for patients that may have previously been treated with a prosthetic nucleus replacement that relied upon the patient's annulus fibrosus. PDR does require at least a bore hole through both of the endplates and removal of nucleus pulposus. Co-pending U.S. patent application Ser. No. 11/586,338 for Spinal Motion Preservation Assemblies (incorporated by reference above) includes a rigid pivot element so some compressive load is borne by the pivot element and some load is borne by the prosthetic nucleus material and the annulus fibrosus may be appropriate for a PDR situation.

Terminology

It is useful to set forth some of the standard medical vocabulary before getting into a more detailed discussion of the background of the present disclosure. In the context of the this disclosure: anterior refers to in front of the spinal column; (ventral) and posterior refers to behind the column (dorsal); cephalad means towards the patient's head (sometimes "superior"); caudal (sometimes "inferior") refers to the direction or location that is closer to the feet. As the present disclosure contemplates accessing the various vertebral bodies and intervertebral disc spaces through a preferred approach that comes in from the sacrum and moves towards the head, proximal and distal are defined in context of this channel of approach. Consequently, proximal is closer to the beginning of the channel and thus towards the feet or the surgeon, distal is further from the beginning of the channel and thus towards the head, or more distant from the surgeon. When referencing delivery tools, distal would be the end intended for insertion into the access channel (whether a trans-sacral access channel or an access channel from another route) and proximal refers to the other end, generally the end closer to the handle for the delivery tool.

Biocompatible as used in this disclosure refers to an absence of chronic inflammation response when or if physiological tissues are in contact with, or exposed to (for example, wear debris) the materials and devices of the present disclosure.

Percutaneous as used in this disclosure simply means through the skin from a paracoccygeal access point on the patient and to the posterior or anterior target point, as in transcutaneous or transdermal, without implying any particular procedure from other medical arts. However, percutaneous access is distinct from a surgical access, and the percutaneous opening in the skin is preferably minimized so that it is less than four centimeters across, preferably less than two centimeters. The percutaneous access pathway is generally axially aligned with the bore extending from the respective anterior or posterior target point through at least one sacral vertebral body and one or more lumbar vertebral body in the cephalad direction as visualized by radiographic or fluoroscopic equipment.

In the context of the present disclosure, the term distraction refers procedurally to an elevation in height that increases the intervertebral disc space resulting from introduction of the motion preservation assembly or prosthetic nucleus device which may be achieved either in the axial deployment of the device itself, or assisted by other processes.

Trans-Sacral Axial Access

Because of the many advantages associates with a minimally invasive, low trauma trans-sacral axial approach, the present disclosure contemplates the use of the trans-sacral axial access to the lumbo-sacral spine. The trans-sacral axial approach (described and disclosed in commonly assigned U.S. Pat. Nos. 6,558,386; 6,558,390; 6,575,979; 6,921,403; 7,014,633, and 7,087,058) has a number of advantages over other routes for delivery of therapeutic devices to motion segments but there are logistical challenges to the delivery and deployment of advanced spinal assemblies via an axial access channel. The process of addressing these challenges impacts certain aspects of the implanted device and obviously impacts the design of the insertion tools.

The trans-sacral axial access method illustrated in FIGS. 1A, 1B, and 1C, eliminates the need for muscular dissection and other invasive steps associated with traditional spinal surgery while allowing for the design and deployment of new and improved instruments and therapeutic interventions, including stabilization, motion preservation, and fixation devices/fusion systems across a progression-of-treatment in intervention.

FIGS. 1A-1C provide an introductory overview of the process with FIG. 1A and FIG. 1B showing the process of "walking" a blunt tip stylet 204 up the anterior face of the sacrum 116 to the desired position on the sacrum 116 while monitored one or more fluoroscopes (not shown). It is useful to have access to both an anterior/posterior (AP) view and a lateral fluoroscopic image. This process moves the rectum 208 out of the way so that a straight path is established for the subsequent steps. FIG. 1C illustrates a representative trans-sacral access channel 212 (also called axial channel) established through the sacrum 116, the L5/sacrum intervertebral disc space, and into the L5 vertebra 216. If therapy is being provided to the L4/L5 motion segment then the access channel 212 would continue through the L5 vertebra 216 through the L4/L5 intervertebral disc space, and into the L4 vertebra 220. Preparation of access channel 212 allows for subsequent delivery of therapeutic devices oriented substantially along the long axis of the spine.

SUMMARY OF THE DISCLOSURE

Aspects of the teachings contained within this disclosure are addressed in the claims submitted with this application upon filing. Rather than adding redundant restatements of the contents of the claims, these claims should be considered incorporated by reference into this summary.

The prosthetic nucleus implants described below include injected prosthetic nucleus material that changes from a flowable to a non-flowable state. The prosthetic nucleus material may be selected to be deformable but not compressible. A prosthetic nucleus implant that conforms to the size and shape created during the removal of the nucleus pulposus with an incompressible material works in unison with the remaining disc nucleus material and the intact annulus fibrosus to distribute loads evenly across the vertebral body endplates regardless of the shape of the prosthetic nucleus implant.

The delivery of membranes of the type referenced above may be facilitated by the use of various inventive tools and methods described in this disclosure.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow. Other systems, methods, features and advantages of the disclosed teachings will be or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the set of figures. The components in the figures are not necessarily to scale, emphasis instead being placed upon illustrating the principles of the disclosure. Moreover, in the figures, like reference numerals designate corresponding parts throughout the different views.

DETAILED DESCRIPTION

First Example

The present disclosure will now be described more fully hereinafter with reference to accompanying drawings in order to disclose selected illustrative implementations of the present disclosure. The teachings of the present disclosure may, however, be embodied in many different forms and should not be construed as limited to the particular implementations set forth herein; rather these implementations are provided so that the disclosure can be thorough and complete, and as part of the effort to convey the scope of the disclosure to those skilled in the art.

Figure 2:
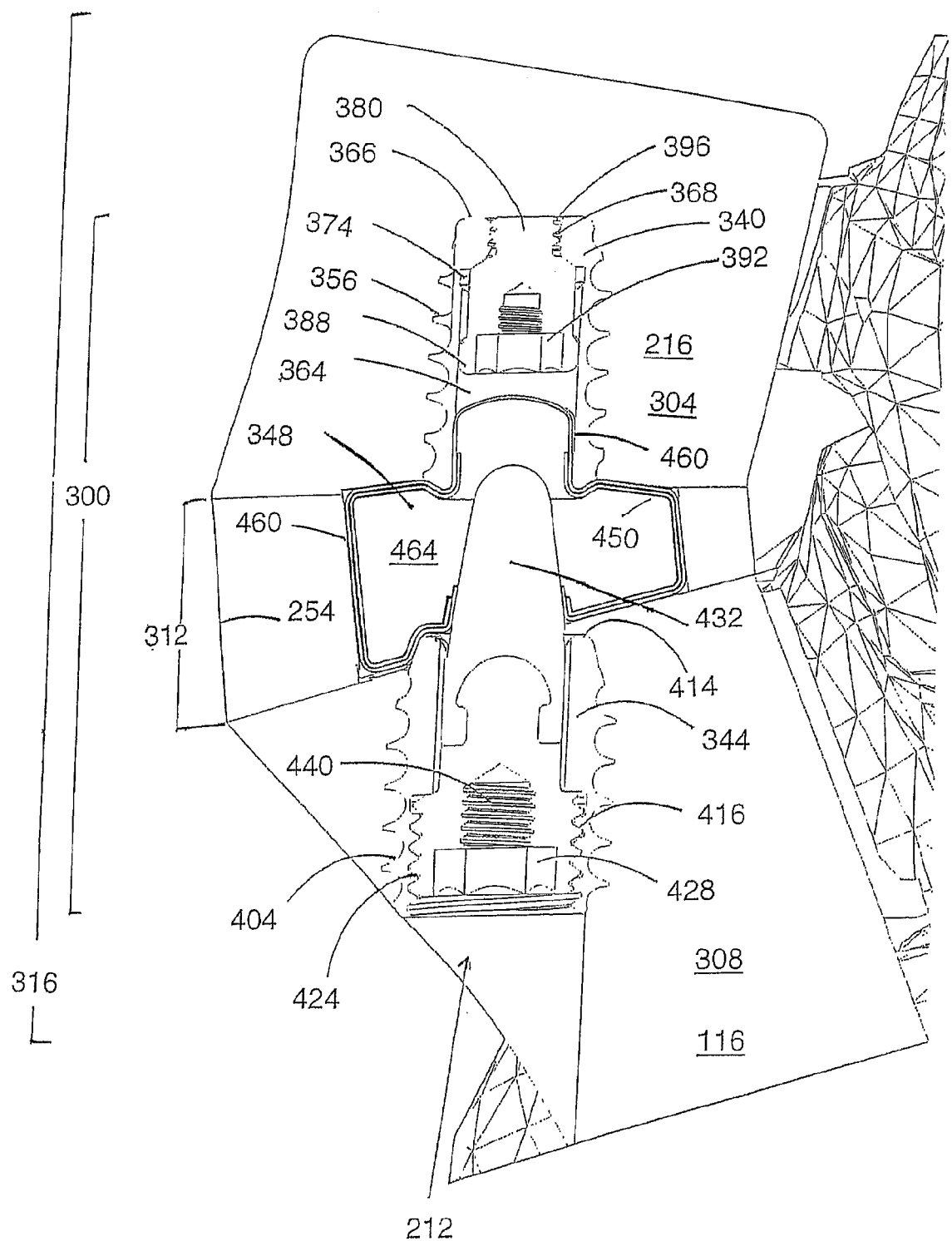
FIG. 2 is a cross section of a multi-membrane prosthetic nucleus in a spinal motion preservation assembly in a L5/S1 motion segment.
Figure 3:
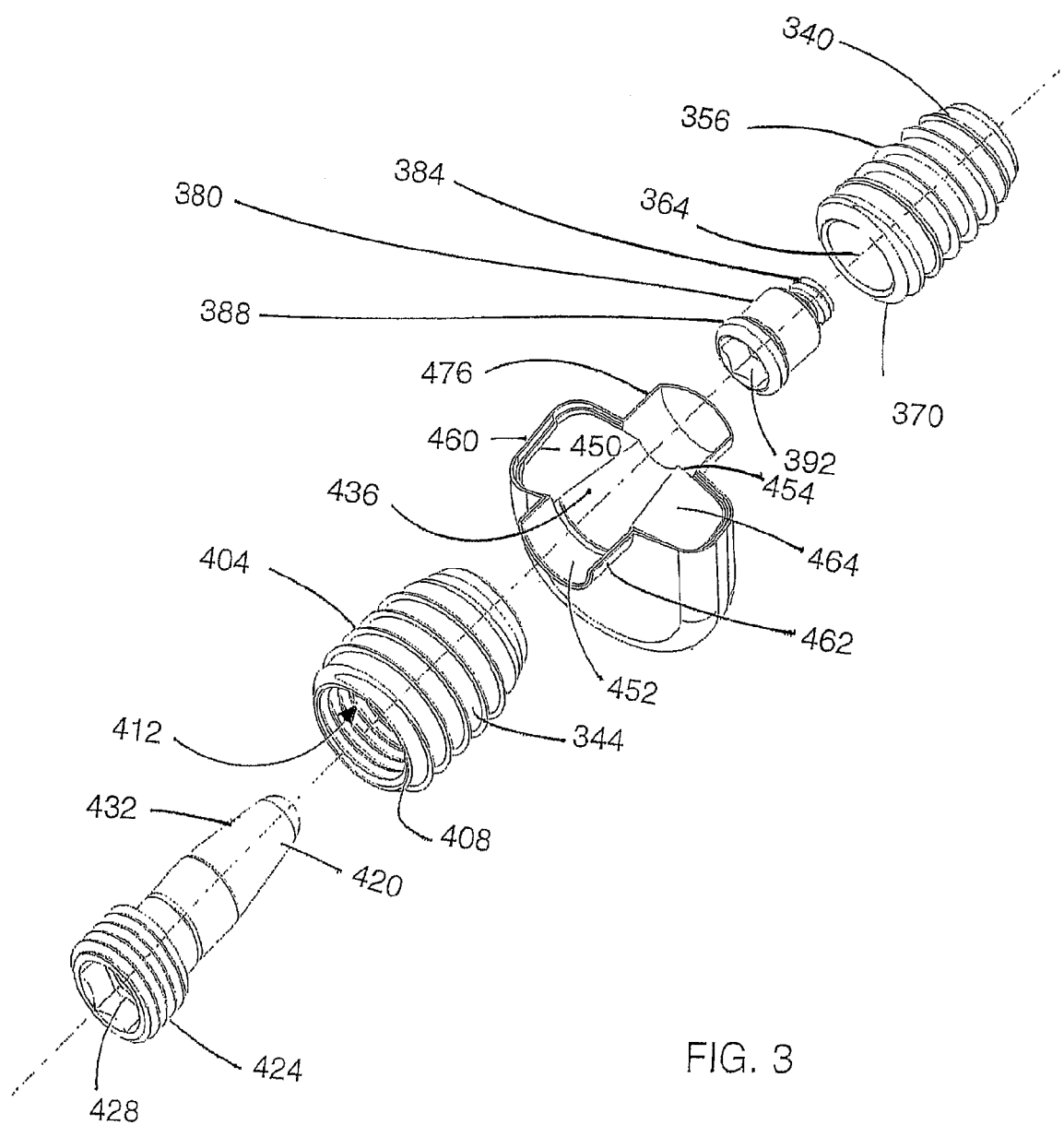
FIG. 3 is a perspective view of an exploded diagram of the spinal motion preservation assembly shown in FIG. 2.
Figure 4:
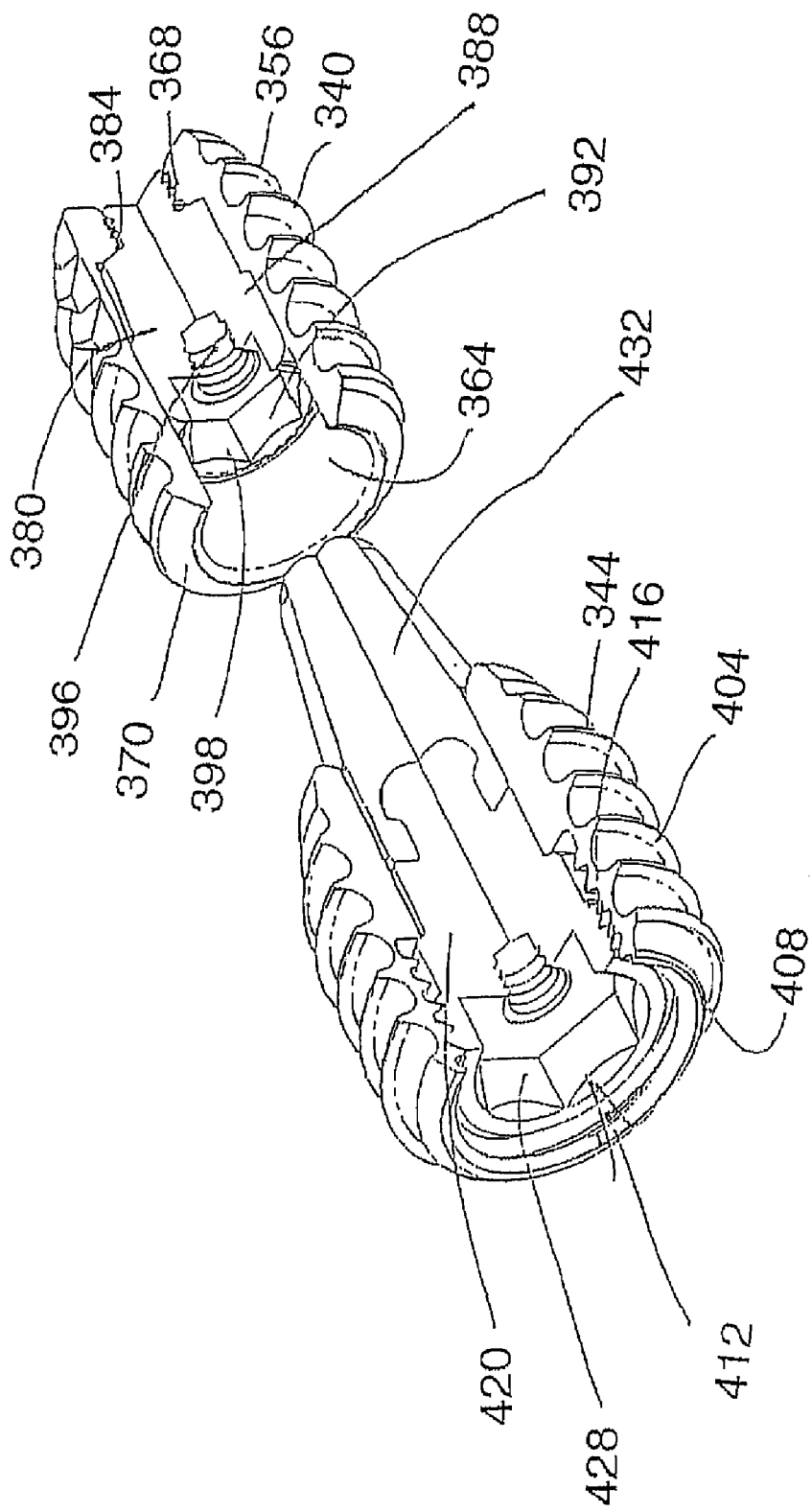
FIG. 4 is a perspective view of the spinal motion preservation assembly shown in FIGS. 2 and 3 with a quarter round removed and without the membranes or the injected prosthetic nucleus material.

In order to avoid the imprecision that can sometimes be introduced into a patent disclosure while discussing many different alternative configurations at once, FIGS. 2-4 start with one very specific embodiment of the present disclosure. In order to provide an overview of the components and their placement with respect to a spinal motion segment, the explanation will start with an overview of an implanted device. Subsequent drawings will provide detail on the delivery and assembly of the device.

FIG. 2 illustrates an implanted motion preservation assembly 300. FIG. 3 provides an exploded diagram that provides another view of the components described in FIG. 2. FIG. 4 is a perspective view of some of the components with a quarter round removed (but excludes the prosthetic nucleus material). In order to avoid undue clutter from having too many reference numbers and lead lines on a particular drawing, some components will be introduced via one drawing and not explicitly identified in every subsequent drawing that contains that component.

Figures 1A, 1B, 1C:
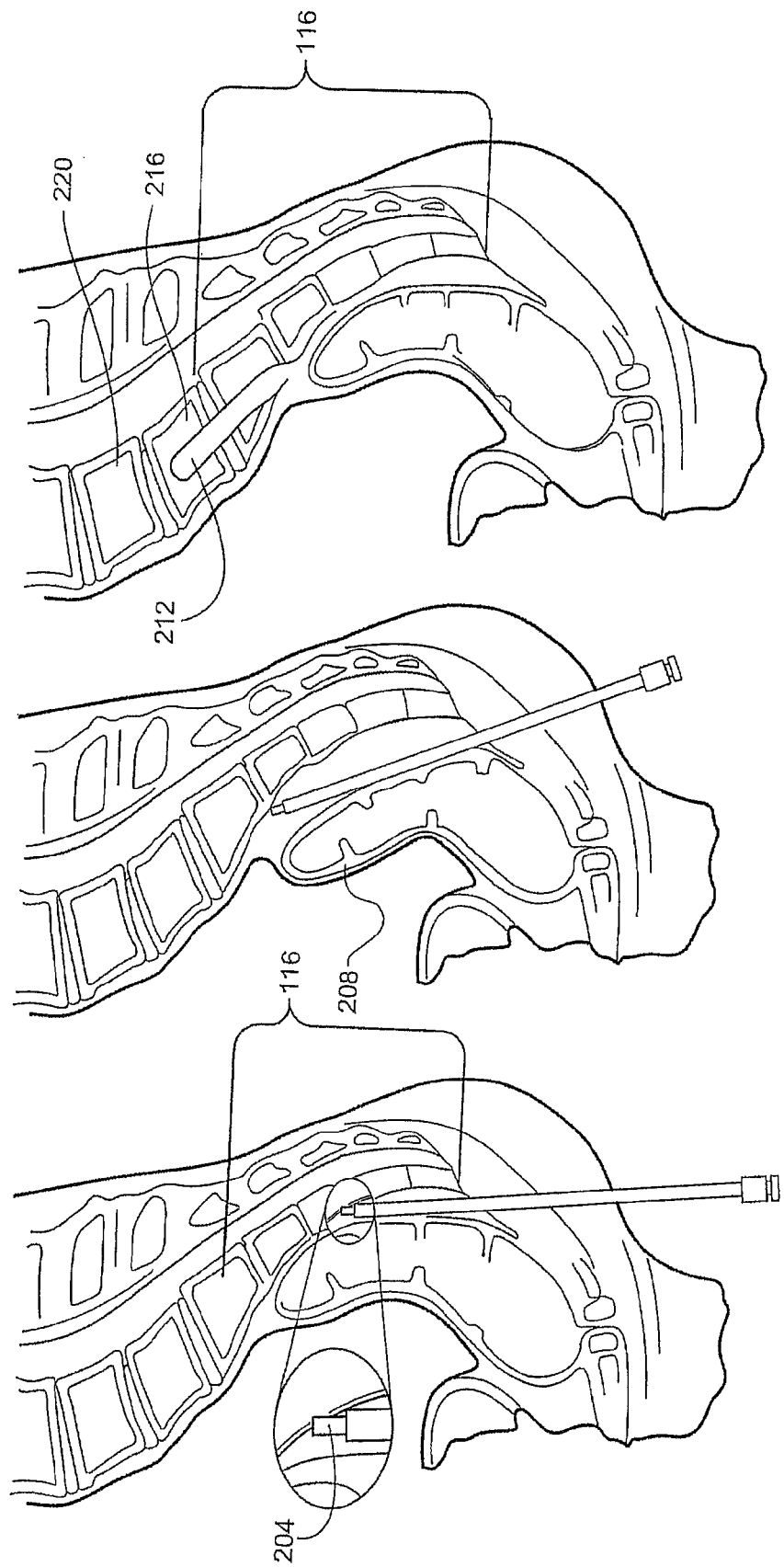
FIGS. 1A, 1B, and 1C review the process of creating a trans-sacral access channel

This motion preservation assembly 300 is implanted into a distal vertebral body 304 and a proximal vertebral body 308. As shown in FIG. 2 by way of example, the distal vertebral body 304 is the L5 vertebra 216 and the proximal vertebral body 308 is the sacrum 116. The deployed motion preservation assembly 300 extends across an intervertebral disc space 312. The motion preservation assembly 300 would be placed in a previously prepared access channel 212 (FIG. 1C). The trans-sacral axial approach left intact the axial walls of the annulus fibrosus 254 (best seen in FIG. 2). Collectively, the distal vertebral body 304, the proximal vertebral body 308 and the intervertebral disc space 312 form a motion segment 316. (as the proximal body in FIG. 2 is the sacrum, only the upper portion of the sacrum is shown within bracketed area 316) The drawings of the vertebral bodies in this figure are not intended to convey anatomical details of the spinal components but to illustrate the placement of the assembled motion preservation assembly 300. In a like manner, other figures in this disclosure are used to disclose specific concepts rather than to convey details of human anatomy. While the example pair of adjacent vertebral bodies used in FIG. 2 are L5 and sacrum (or to be more specific S1), other motion segments can receive a spinal motion preservation assembly using a trans-sacral axial approach. It is believed that the second most common location for use of a spinal motion preservation assembly via an axial trans sacral approach will be between the L4 and L5 vertebrae 220 and 216 (See FIG. 1C), but other motion segments may benefit from such devices.

The major components of the motion preservation assembly 300 include the distal bone anchor 340 (anchored in the superior, or distal vertebral body), proximal bone anchor 344 (anchored in the inferior, or proximal vertebral body), prosthetic nucleus 348 including outermost membrane 460, innermost membrane 450 and injected prosthetic nucleus material 464.

As discussed in greater detail below, additional membranes could exist between the outermost membrane 460 and the innermost membrane 450. These additional membranes may be referenced as intermediate membranes (none shown in FIG. 2). The individual intermediate membranes may have properties like an innermost membrane 450 or like an outermost membrane 460. The innermost membrane 450 is expandable in reaction to the inflation pressure of the prosthetic nucleus material 464 to assume the shape of the prosthetic nucleus 348. In contrast, while the outermost membrane 460 may expand a measurable amount in reaction to the inflation pressure of the prosthetic nucleus material 464 within the innermost membrane 450, the outermost membrane grows larger primarily through unfolding or unfurling from a shape assumed by the outermost membrane 460 for delivery to the interior of the intervertebral disc space 312.

The distal bone anchor 340 shown in FIG. 2 has a set of external threads 356. Advantageously, the set of external threads 356 can include a chip breaker section 360 (not visible in FIG. 3 but see FIG. 9) at the distal end of the distal bone anchor 340 to facilitate the starting of cutting a thread path into the distal vertebral body 304. A chip breaker section 360 is a discontinuity in the thread that allows chips to break off as the thread path is cut. The access channel 212 (FIG. 1C) is created into the distal vertebral body 304, with the diameter of the access channel 212 at the distal vertebral body 304 typically approximately equal, or slightly less than, the minor diameter of the set of external threads 356.

The distal bone anchor 340 has a cavity 364 (best seen in FIG. 3) running from the distal face 366 of the distal bone anchor 340 to the proximal face 370 (FIG. 2) of the distal bone anchor 340. In this context, a face is the three-dimensional surface of the part as viewed from that side, akin to the six three-dimensional faces of die from a pair of dice. The cavity 364 is not of uniform cross section and serves several purposes. The distal end of the cavity 364 extends to the distal face 366 of the distal bone anchor 340 such that the cavity can be used to allow the distal bone anchor 340 to be deployed over a guide wire (not shown). The cavity 364 includes an internal threaded section 368 which can be engaged by a retention rod (See element 2300 in FIG. 13) as described below. This same internal threaded section 368 may be subsequently engaged by a set of external threads 384 on a distal plug 380. The distal plug 380 has a shoulder 388 that contacts a corresponding section of the distal bone anchor 340. The distal plug 380 has a driver engagement section 392 which is typically a female hex fitting that may be torqued by an appropriately sized hexagonal driver. A set of internal threads 396 within distal plug 380 may be engaged by a retention rod during the process of delivering the distal plug 380. A cavity 398 open at the proximal end of the distal plug 380 exposes the set of internal threads 396 and the driver engagement section 392.

The distal bone anchor 340 is adapted to be driven by a polygonal driver received in the proximal end of the cavity 364 in the distal bone anchor 340. In this implementation, the distal bone anchor 340 has a female hex section 374 (best seen in FIG. 4).

The cavity 364 in the distal bone anchor 340 shown in FIG. 2 is partially filled with the distal plug 380. The distal plug 380 does not extend beyond the proximal face 370 of the distal bone anchor 340 into the intervertebral disc space 312.

The proximal bone anchor 344 has a set of external threads 404. The proximal bone anchor 344 has a cavity 412 (best seen in FIG. 3) that runs from the proximal face 408 (best seen in FIG. 4) of the proximal bone anchor 344 to the distal face 414 (best seen in FIG. 2) of the proximal bone anchor 344. The cavity 412 is not uniform in cross section. A portion of the cavity 412 has a set of internal threads 416.

In the implementation shown in FIGS. 2-4, the proximal bone anchor cavity 412 contains a proximal plug 420 that has a set of external threads 424 that engage with the set of internal threads 416 to allow torque from a driver imparted to a driver engagement section 428 to rotate the proximal plug 420 relative to the proximal bone anchor 344 to axially advance the proximal plug 420. A set of internal threads 440 exist within the proximal plug 420 for use with a retention rod (sometimes called a retention tube). The proximal plug 420 may include optional axial thread grooves in the external threads 424 to make the external threads 424 less susceptible from problems arising from small amounts of prosthetic nucleus material (such as silicone) which may get into the internal threads 416 in the proximal bone anchor 344.

Note that this process allows for the selective loading of the membranes by the insertion of the distal section 432 of the proximal plug 420 into the now non-flowable prosthetic nucleus material 464. The sizing of the distal section 432 relative to the anticipated size and shape of the anticipated void allows for the application of expansion forces as the prosthetic nucleus 348 receives additional material from the insertion of the distal section 432 of the proximal plug 420. This insertion may be used to selectively increase the volume of the prosthetic nucleus. Optionally, the external threads 424 on the proximal plug 420 and the corresponding internal threads 416 on the proximal bone anchor 344 may be implemented with a relatively fine pitch compared with the external threads 404 on the proximal bone anchor 344 so that torque applied to the proximal plug 420 is likely to rotate the proximal plug 420 relative to the proximal bone anchor 344 rather than cause the proximal bone anchor 344 to rotate relative to the proximal vertebral body 308.

Advancing the proximal plug 420 causes a distal section 432 of proximal plug 420 to advance into a void 436 (best seen in FIG. 3) created during the process of injecting the prosthetic nucleus material 464. Optionally, the surgeon may be provided with proximal plugs of different lengths so that a longer proximal plug may be used in situations with wider intervertebral disc spaces.

Through this two step process of injecting the flowable prosthetic nucleus material 464 then filling the void 436 created as part of that process with the distal end of a plug, the amount of material added by the plug may be selected as needed to adjust the fullness of the prosthetic nucleus. Thus, a surgeon may choose not only a longer plug but possibly a broader or otherwise a more voluminous plug to alter the fullness of the prosthetic nucleus. Likewise the degree to which the proximal plug 420 is advanced may be used to control the fullness of the prosthetic nucleus.

As shown in FIG. 2, the proximal plug 420 may extend through the intervertebral disc space 312 and extend partially into the cavity 364 in the distal bone anchor 340. Note that the distal ends of the innermost membrane 450 and outermost membrane 460 are shown in this figure as within the cavity 364. The proximal ends of the innermost membrane 450 and outermost membrane 460 are shown in FIG. 2 inverted and pushed up and into the intervertebral disc space 312. As the proximal end 462 of the outermost membrane 460 is longer than the proximal end 452 of the innermost membrane 450, the outermost membrane 460 is pushed further into the void. The lengths of the proximal and distal ends 452 and 454 of the innermost membrane 450 may be longer if the membrane end is pulled free from the retaining rings rather than torn during the removal of the membrane inserter assembly discussed below.

FIG. 3 shows the closed cap portion 476 of the outermost membrane 460. FIG. 3 also shows the open distal end 454 of the innermost membrane 450 although it may frequently extend up into the closed cap portion 476. FIG. 3 shows the open proximal end 452 of the innermost membrane 450 before inversion by the insertion of the proximal plug 420. The open proximal end 462 of outermost membrane 460 is also shown. In most cases, the open proximal end 462 of the outermost membrane 460 would actually extend beyond the open proximal end 452 of the innermost membrane 450 in the proximal direction before being inverted by the proximal plug 420.

The proximal plug 420 may have a distal section 432 that is made of a material that is different than the proximal end of the proximal plug 420. The distal section 432 may be made of the same material as the injected prosthetic nucleus material 464. Often the material used for the distal section 432 will be similar but not the same as that of injected prosthetic nucleus material 464. For example, a flowable silicone used for the injected prosthetic nucleus material 464 may be adapted to cure quickly and thus have catalysts or other agents present to a greater degree than in the material used for the distal section 432. Often the distal section 432 of the proximal plug 420 will be firmer (for example—have a durometer value of 50 rather than 20) than the injected prosthetic nucleus material 464 even after that material has changed so it is no longer flowable. This added firmness is useful for inserting the distal section 432 into the irregularly shaped void 436 in the prosthetic nucleus material 464 and for pushing the proximal ends 452 and 462 of the membranes into the void 436.

Process of Implanting Device

A. Overview

Figure 5:
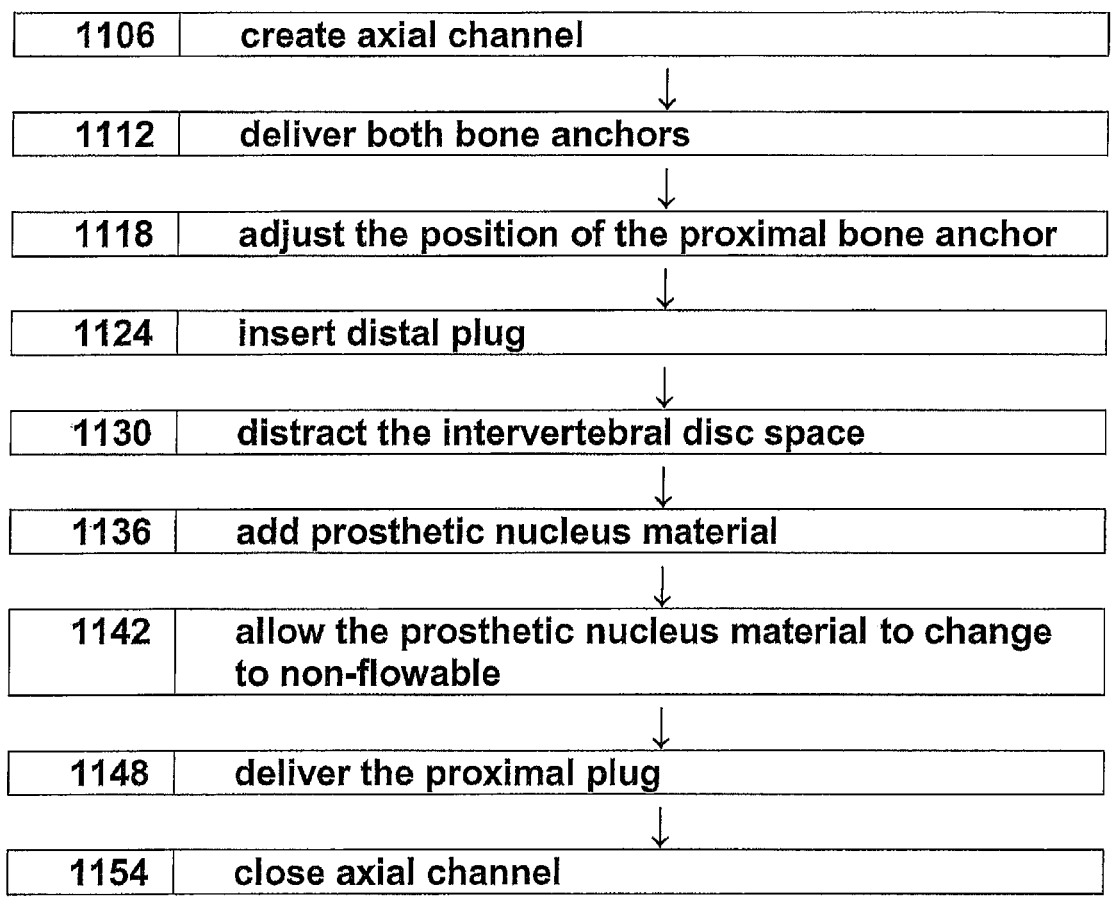
FIG. 5 is a high level flow chart that is useful to introduce the overall sequence of events for delivery of a spinal motion preservation assembly of the type illustrated in FIGS. 2-4.
Figures 6, 6A:
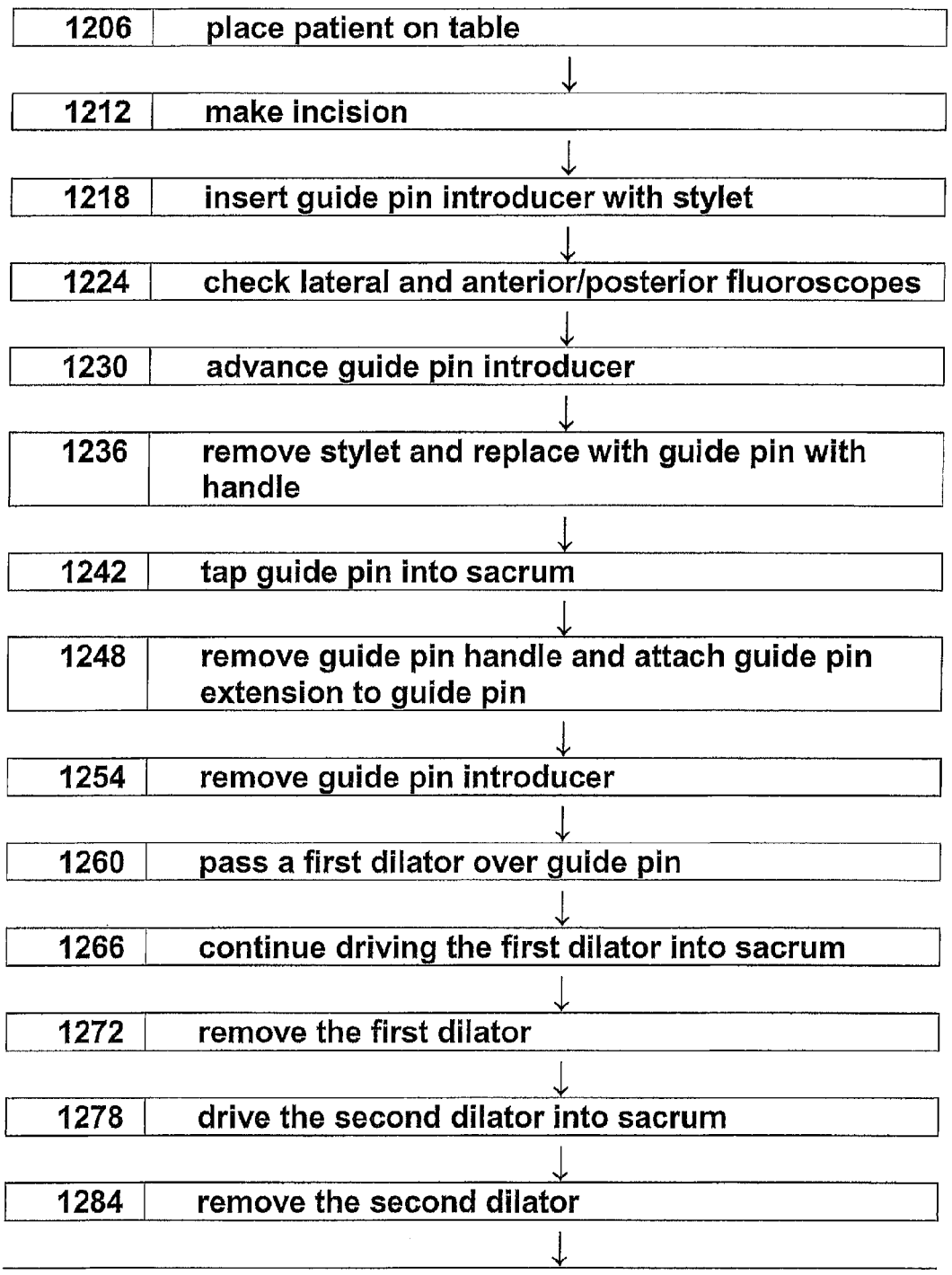
FIG. 6 provides a more detailed description of one set of steps that could be used to prepare an access channel via an anterior trans-sacral axial approach for use with distal and proximal anchors.
Figure 6C:
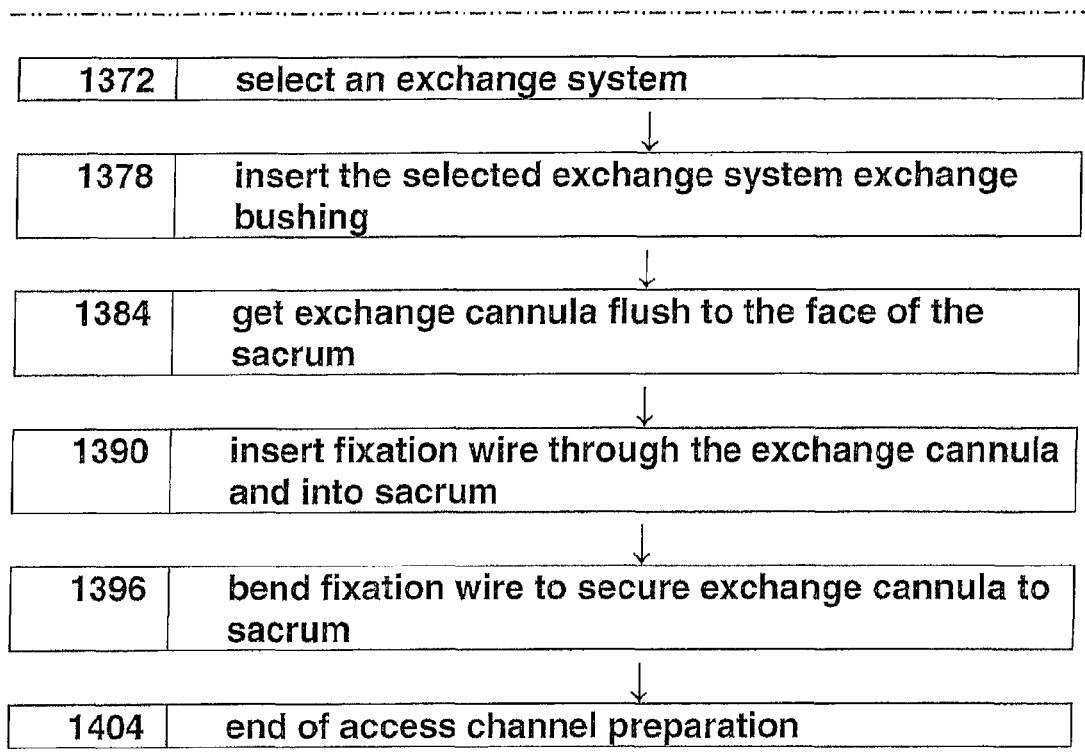
Figure 7B:
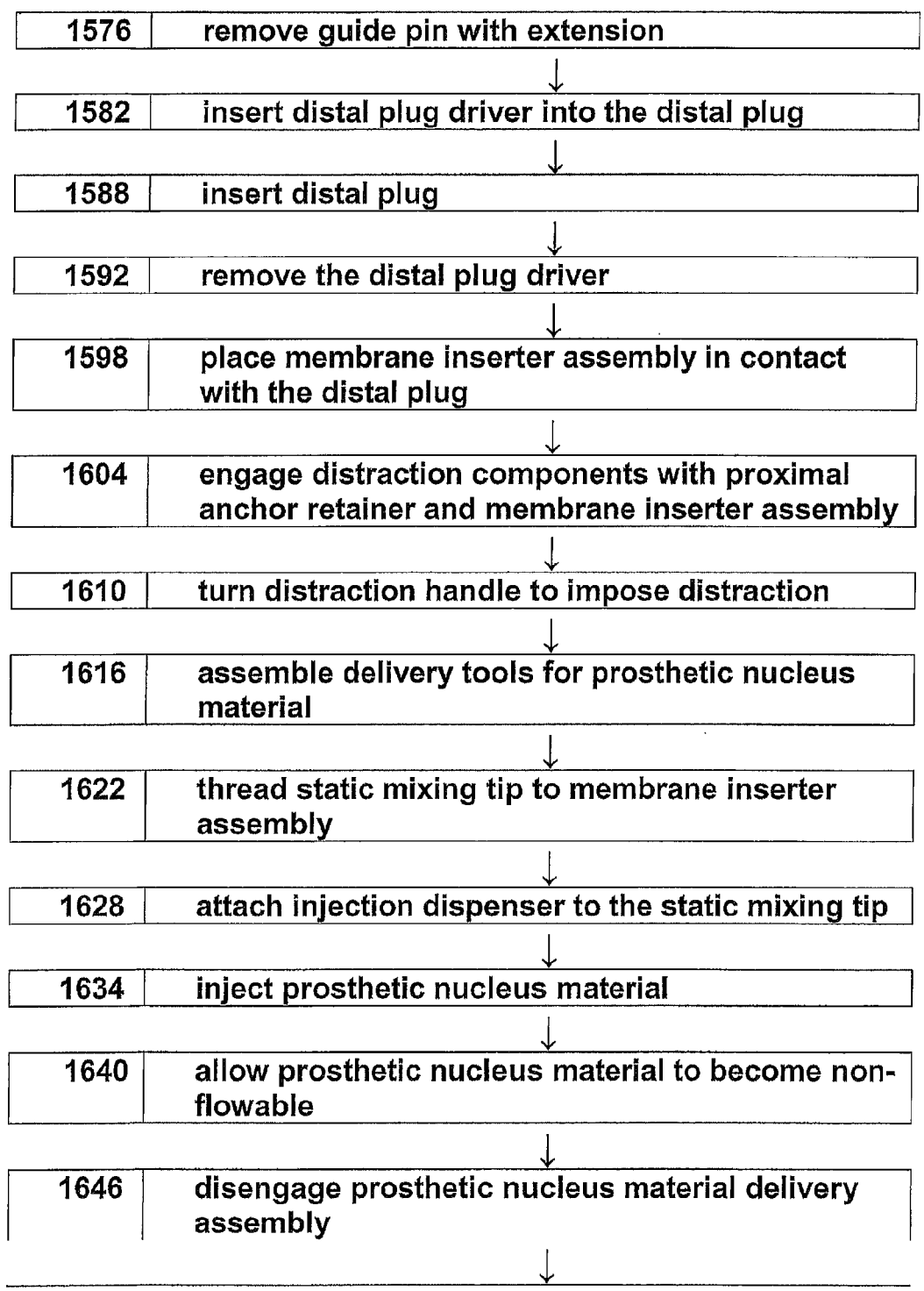
FIG. 7 is a flow chart for one set of steps to deploy a motion preservation assembly of the type show in FIGS. 2-4.
Figure 7C:
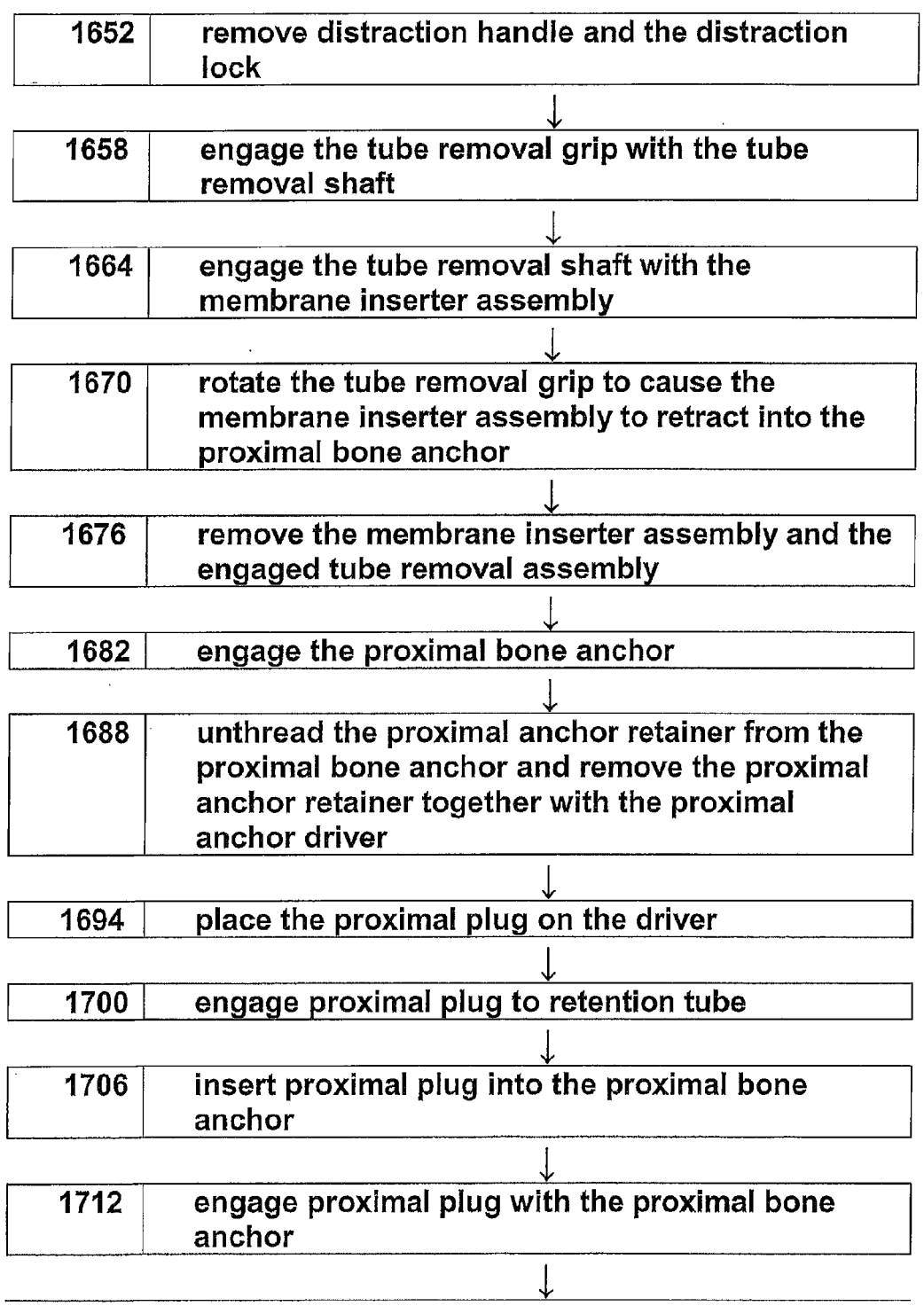
Figure 7D:
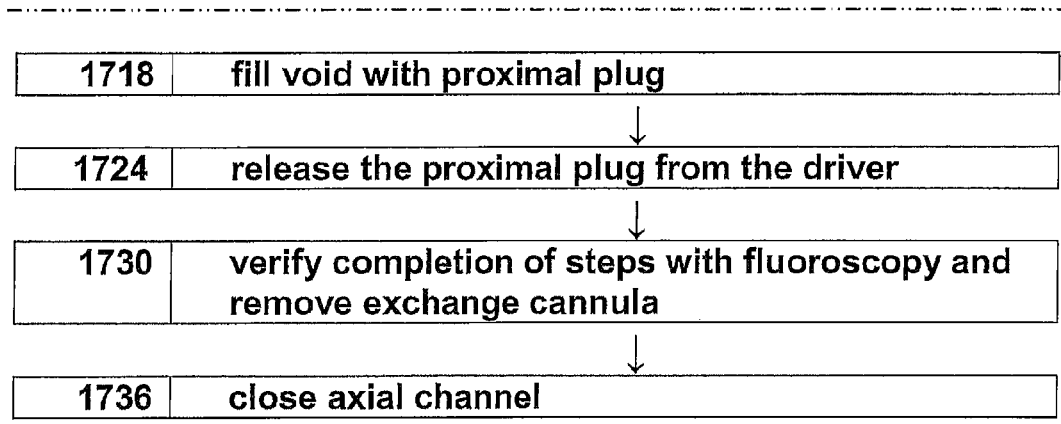

FIG. 5 is a high level flow chart that is useful to introduce the overall sequence of events for delivery of a spinal motion preservation assembly 300 of the type illustrated in FIGS. 2-4. This flow chart and the more detailed flow charts contained in FIGS. 6 and 7 provide details that are descriptive of delivery of a one particular implementation of the teachings of this disclosure to the L5/S1 motion segment via a specific route. Thus, while there are many possible variations of the ways that spinal motion preservation assemblies may be implemented, it would be confusing to attempt to simultaneously explain the delivery process for many different implementations of a spinal motion preservation assembly. Hence, it is appropriate to focus and describe a specific process for one particular spinal motion preservation assembly. This specificity is thought to be useful in illustrating the interaction between specific portions of the spinal motion preservation assembly components and the various drivers used in the delivery process so that one of ordinary skill in the art could modify both the components and the drivers as needed to deliver other spinal motion preservation assemblies incorporating one or more teachings of the present disclosure. With that understanding of the purpose of these flow charts, attention is directed to FIG. 5.

1106—Create access channel 212. This process will be described in more detail in connection with FIG. 6.

1112—Deliver both bone anchors (340 and 344) to the pair of vertebral bodies and adjust the position of the distal bone anchor 340 relative to the distal vertebral body 304. As described below, in this implementation, the two anchors are initially delivered by timed delivery on a dual anchor driver. As the position of the distal bone anchor 340 is adjusted, the dual anchor driver is also engaged with the proximal bone anchor 344. Remove the dual anchor driver.

1118—Adjust the position of just the proximal bone anchor 344 with a proximal bone anchor driver.

1124—Insert distal plug 380 using distal plug inserter into distal bone anchor 340

1130—Distract the intervertebral disc space 312 between the distal vertebral body 304 and the proximal vertebral body 308 by forcing an increase in distance between the distal bone anchor 340 and the proximal bone anchor 344. Increasing the distance between the two bone anchors increases the distance between the proximal vertebra and the distal vertebra as they are attached to the two bone anchors. If there is not a clinical need for a distraction, then this step may be omitted 1136—Add prosthetic nucleus material 464 to fill the space in the intervertebral disc space 312 but not a portion of the intervertebral disc space between the proximal bone anchor 344 and the distal bone anchor 340 as that space is occupied during filling by a portion of the device used to fill the prosthetic nucleus. Thus, removal of the device will leave a void 436 in the injected prosthetic nucleus material 464.

1142—Allow the prosthetic nucleus material 464 to change from flowable to non-flowable so that the prosthetic nucleus can substantially maintain the distraction after the distraction tool is removed and bear the load applied to the motion segment. Since the patient is likely to be in a horizontal position during this procedure, the full loading of the prosthetic nucleus will not come until well after the proximal plug 420 is inserted and the procedure is completed.

1148—Deliver the proximal plug 420 to the proximal bone anchor 344 and drive the distal section 432 of the proximal plug 420 into the void 436 left in the prosthetic nucleus material 464.

1154—Close access channel 212.

B. Details on the Creation of an Access Channel

After that general introduction to the process, FIG. 6 provides a more detailed description of one set of steps that could be used to prepare an access channel 212 via an anterior trans-sacral axial approach for use with distal and proximal anchors. Note that although FIG. 6 describes a process to provide an access channel for the delivery of a spinal motion preserving assembly 300 to the L5/S1 motion segment, the use of spinal motion preservation assemblies is not limited to solely that motion segment. As much of the process for preparing the access channel is the same or similar to processes described in previous applications for this assignee, the steps are assumed to be relatively self-explanatory but are provided here as an outline that would be meaningful to one of ordinary skill in the art. As noted below, spinal motion preservation assemblies could be implemented with only an anchor in the proximal vertebral body 308 or without an anchor at all. As discussed below, in an application without a proximal bone anchor 344, a proximal plug could be threadedly engaged directly with the proximal vertebral body 308. Those of ordinary skill in the art could modify the details provided in FIG. 6 and the related text to modify the access channel preparation process accordingly.

Tools relevant to preparation of the access channel including tissue extractors are described in co-pending and commonly assigned U.S. patent application Ser. No. 10/971,779 for Access Instrumentation Systems.

1206—Place patient on table in a prone position. As would be appreciated by one of skill in the art, the patient may be positioned on a Jackson table or positioned with sand bags as needed to get the desired alignment.

1212—Make longitudinal incision just below and lateral to the coccyx using a scalpel, incision length of approximately 2 centimeters.

1218—Insert guide pin introducer with stylet under fluoroscopy into the presacral space.

1224—Check lateral and anterior/posterior fluoroscopes to verify location of guide pin introducer tip. Fluoroscopes will be consulted as needed for the remainder of procedure to continually verify instrument position and trajectory when necessary using lateral and anterior/posterior fluoroscope visualization.

1230—Advance guide pin introducer until it reaches desired entry point on sacral face. As noted above, the sacrum in an adult is a fused set of vertebrae given individual names S1 to S5. S1 is the most cephalad of these vertebrae.

1236—Remove stylet and replace with guide pin with handle.

1242—Determine proper trajectory and when aligned, tap guide pin into sacrum with slap hammer until guide pin crosses L5/S1 intervertebral disc space and secures itself in L5 vertebral body 216.

1248—Remove guide pin handle and attach guide pin extension to guide pin.

1254—Remove guide pin introducer making sure that guide pin remains in place.

1260—Pass a first dilator over guide pin and begin driving dilator into the sacrum using the slap hammer over the guide pin. As will be appreciated by those of skill in the art, it is a known process to use a series of dilators of increasing diameter in medical procedures. The sizes of the dilators in a set and the number of dilators are partially based on the ultimate diameter of the working cannula needed for the process.

1266—Continue driving the first dilator into sacrum until the tip reaches the endplate of the sacrum just below the L5/S1 intervertebral disc space.

1272—Remove the first dilator making sure guide pin remains in position and replace with a second, wider dilator.

1278—Drive the second dilator into sacrum using slap hammer until tip reaches the endplate of the sacrum just below the L5/S1 intervertebral disc space.

1284—Remove the second dilator making sure guide pin remains in position and replace with a third dilator with sheath, the third dilator being wider than the second dilator.

1290—Drive the third dilator with sheath into sacrum using slap hammer until tip reaches the endplate of the sacrum just below the L5/S1 intervertebral disc space 312.

1296—Remove the third dilator body leaving sheath in place and verifying that guide pin remains in position as well.

1302—Insert a first cannulated drill over the guide pin and into the third dilator sheath.

1308—Twist drill through the sacrum 116 and into L5/S1 disc space and then remove drill leaving guide pin in position.

1314—Insert the third dilator body into its sheath and remove sheath from sacrum leaving guide pin in position.

1320—Pass a fourth dilator with sheath over guide pin and drive into sacrum 116 using the slap hammer until tip is in L5/S1 disc space.

1326—Remove the fourth dilator body leaving the sheath in place.

1332—Remove guide pin with extension.

1338—Insert second drill into the sheath for the fourth dilator and drill through sacrum into L5/S1 disc space. Remove drill.

1342—Perform nucleectomy on L5/S1 disc space using radial cutters and tissue extractors being careful to maintain cartilage and endplates. Cutters well suited for this task are described in co-pending and commonly assigned U.S. patent application Ser. No. 11/712,548 for Cutter for Preparing Intervertebral Disc Space. While cutters that promote abrasion of the endplates are preferred when preparing a disc space for fusion, cutters may be selected that avoid abrading the endplates when preparing the disc space for a motion preservation therapy. The nucleectomy may be only partial, that is the nucleectomy may leave original nucleus pulposus material as the prosthetic nucleus apparatus is adapted to work in concert with the original nucleus pulposus material to transfer load to the nucleus fibrosus.

1348—Optional step: use small radial cutter to countersink endplate of sacrum to remove any pieces of endplate that could damage a membrane during inflation. This optional step may reduce the chance of adverse interaction between bone splinters and the membrane by removing any bone splinters around the perimeter of the newly created bore hole.

1354—Insert the first cannulated drill through sheath for the fourth dilator and drill into L5 216 approximately ⅔rds of the way through the L5 vertebral body. Remove drill. As noted in Step 1348, one may optionally countersink the endplate of the L5 vertebral body although this is apt to be less needed due to the direction of drilling.

1360—Place guide pin with extension into access channel 212.

1366—Pass the fourth dilator body over the guide pin with extension and into the sheath in order to facilitate the removal of the dilator sheath for the fourth dilator body while making sure the guide pin with extension stays in position.

1372—Select an exchange system based on the angle between the trajectory and the sacral face (for example choosing between an exchange system with a 30 degree angle or one with a 45 degree angle). As best seen in FIG. 1C, the anterior face of the sacrum 116 is sloped. Not surprisingly, it is helpful to have a system that approximates the slope in the exchange cannula intended to contact the anterior face of the sacrum to establish an exchange cannula that protects components during insertion into the access channel 212.

Figure 8:
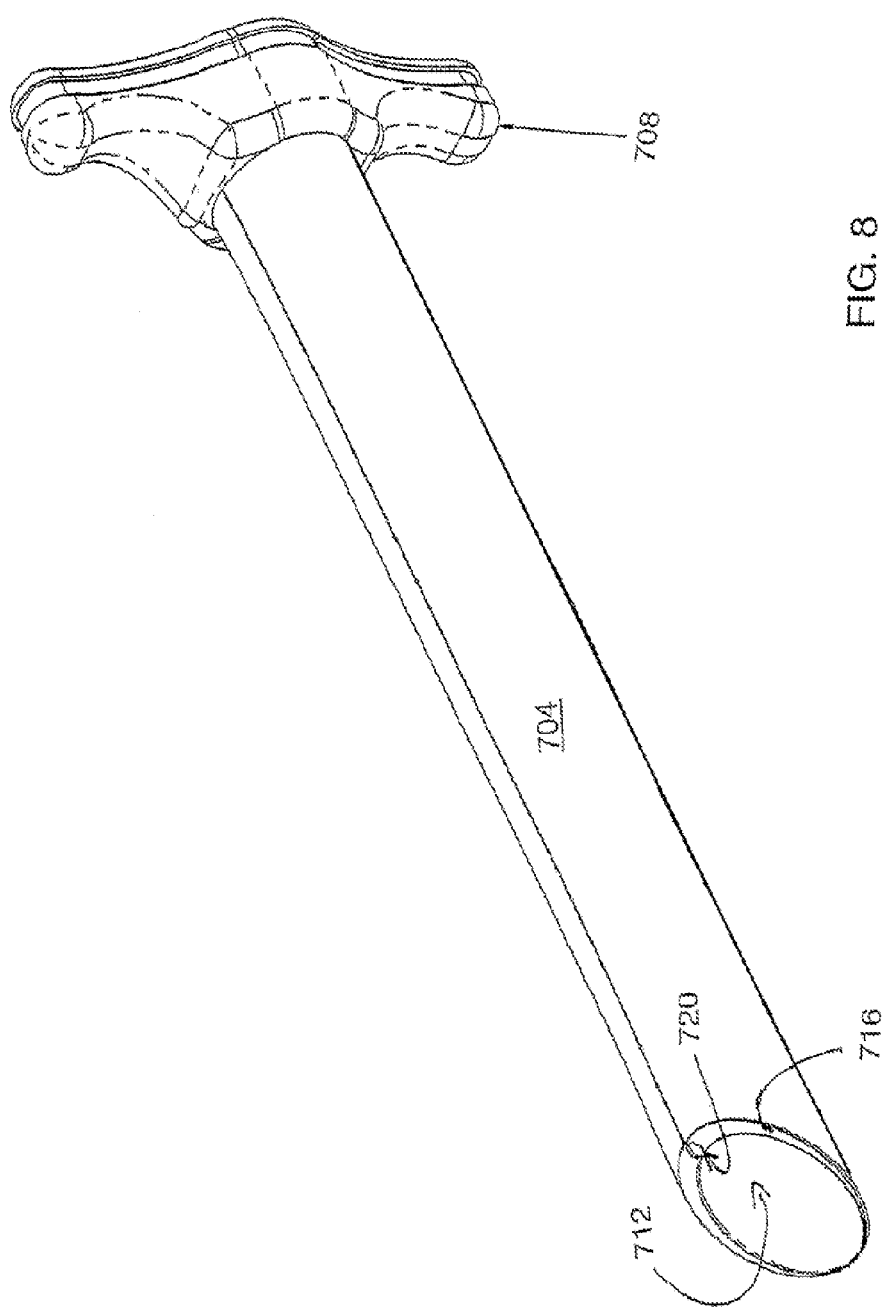
FIG. 8 is a perspective view of exchange cannula 704.

FIG. 8 is a perspective view of exchange cannula 704. The exchange cannula 704 has a handle 708, a main cannula 712 that runs from the handle 708 to the angled distal face 716. In this case the distal face 716 is sloped at 45 degrees. A channel 720 runs along one wall of the exchange cannula 704 and through the handle 708 so that the exchange cannula 704 can be pinned to the sacrum 116 to prevent the exchange cannula 704 from sliding down the anterior wall of the sacrum 116, as described and disclosed in co-pending and commonly assigned U.S. patent application Ser. No. 11/501,351 (incorporated by reference above).

1378—Insert the selected exchange system exchange bushing over the guide pin into the sacral bore.

1384—Pass chosen exchange cannula 704 over exchange bushing and get exchange cannula flush to the face of the sacrum.

1390—Insert fixation wire through the exchange cannula 704 and into sacrum 116 using conventional methods such as a wire driver, slap hammer, or other suitable method.

1396—Bend fixation wire to secure exchange cannula 704 to sacrum 116 and remove exchange bushing.

1404—End of access channel 212 preparation.

C. Delivery of Spinal Motion Preservation Apparatus

After the access channel is prepared, the process of delivering a spinal motion preservation assembly 300 as shown in FIGS. 2-4 proceeds as described in FIG. 7.

C.1 Anchor Insertion

Figure 9:
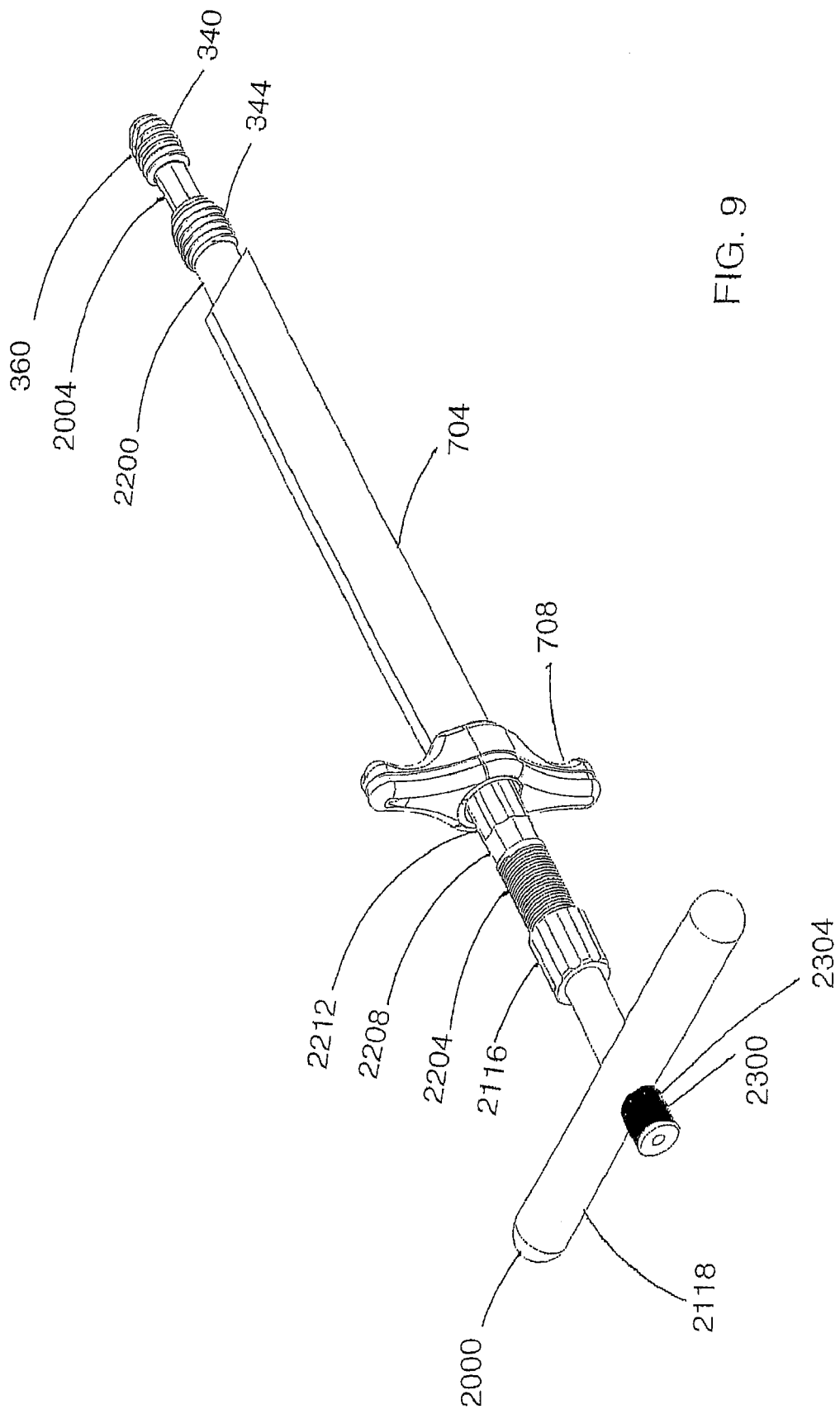
FIG. 9 is a perspective view looking towards the distal direction of a dual anchor driver 2000, proximal anchor retainer 2200 and exchange cannula 704.

This portion of the process references FIG. 9 showing a perspective view of a dual anchor driver 2000, proximal anchor retainer 2200 and exchange cannula 704 looking towards the distal direction. Starting from the distal end, the following components of interest are visible. Distal bone anchor 340 with chip breaker section 360. Distal end of the insertion driver shaft assembly 2100 (shown in FIG. 10).

Figure 10:
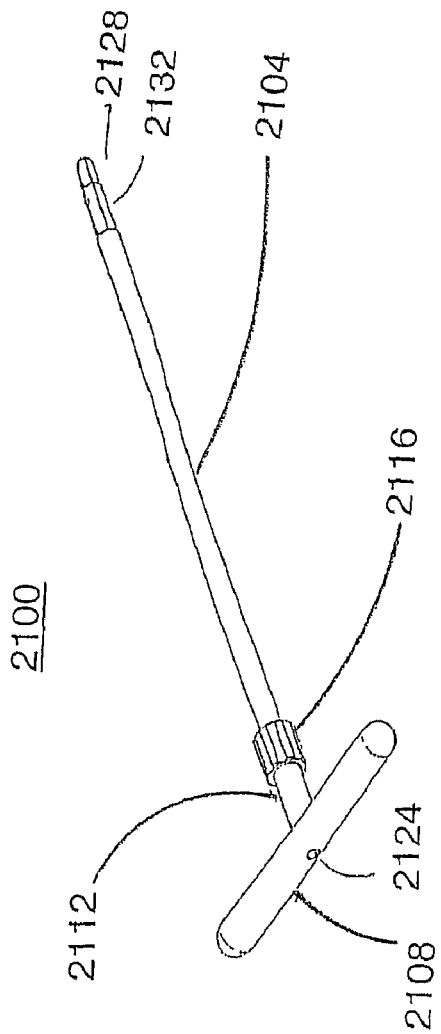
FIG. 10 is a perspective view of the insertion driver assembly 2100.

Moving to FIG. 10, the insertion driver shaft assembly 2100 has an insertion driver shaft 2104, insertion driver handle 2108, insertion driver lock stop 2112, and insertion driver retainer lock 2116.

Figure 11:
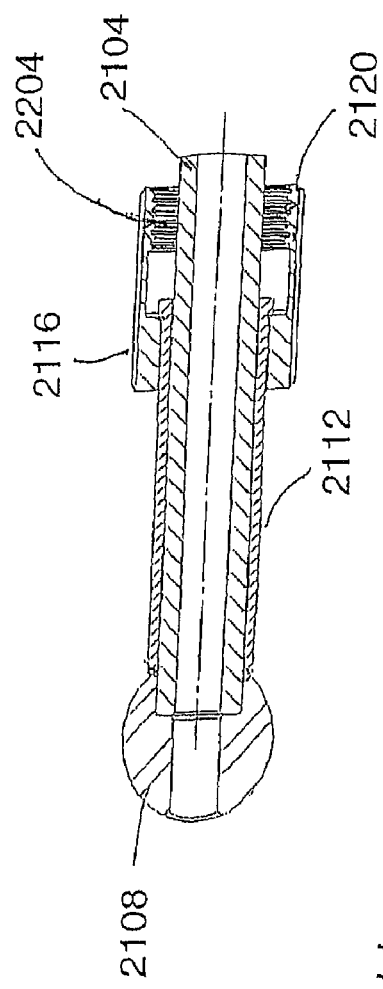
FIG. 11 is an enlarged view of the proximal end of the insertion driver shaft assembly 2100.
Figure 12:
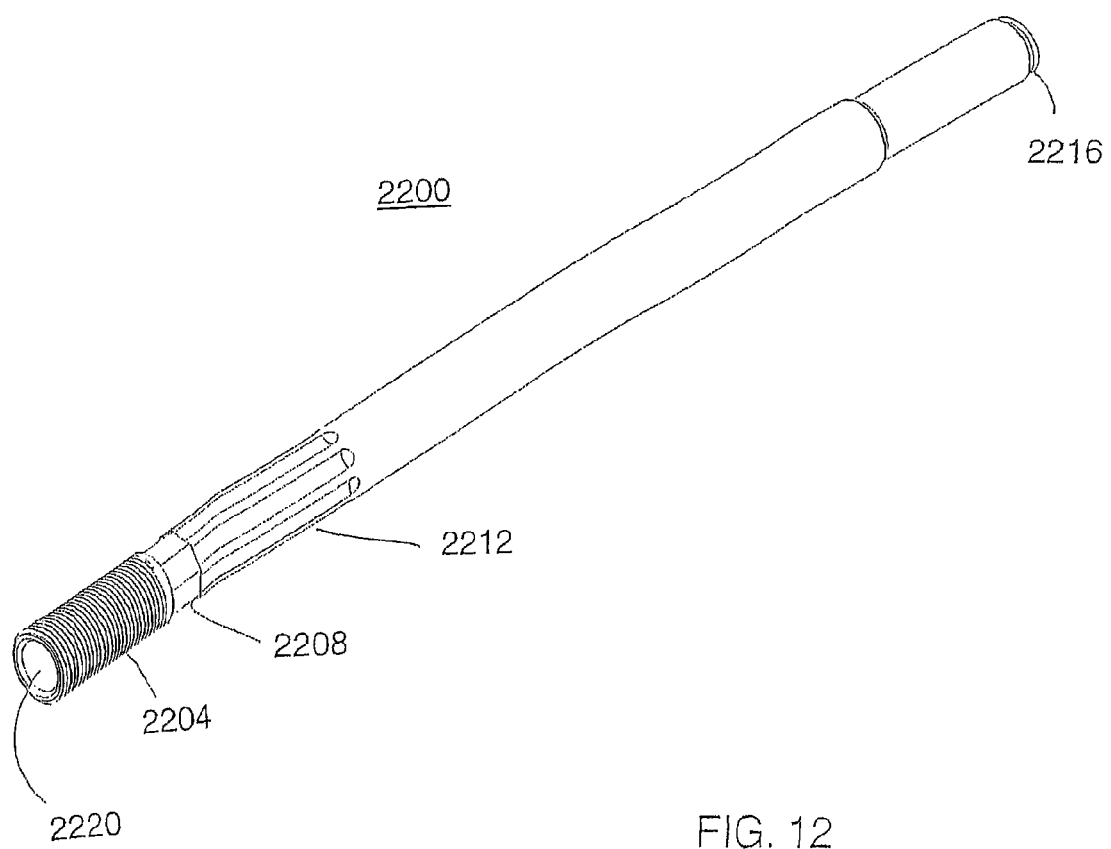
FIG. 12 is a perspective view of proximal anchor retainer 2200.

FIG. 11 is an enlarged view of the proximal end of the insertion driver shaft assembly 2100 including the engagement between the internal threads 2120 on the retainer lock 2116 and the proximal threads 2204 on the proximal anchor retainer 2200 shown in FIG. 12. The distal end of the insertion driver shaft assembly 2100 has a distal anchor driver section 2128 for the distal bone anchor 340 and a proximal anchor driver section 2132 for the proximal bone anchor 344.

FIG. 12 is a perspective view of the proximal anchor retainer 2200 including proximal threads 2204, polygonal section 2208, grip 2212, distal threads 2216, and cavity 2220.

Returning to FIG. 9, much of the proximal anchor retainer 2200 is within exchange cannula 704. Note that the wire within the channel 720 (see FIG. 8) that holds the exchange cannula 704 to the sacrum 116 is not shown in FIG. 9. The proximal end of the exchange cannula 704 has handle 708.

The proximal portion of the proximal anchor retainer 2200 is visible in FIG. 9 with a portion of the grip 2212, polygonal section 2208, and proximal threads 2204. Insertion driver retainer lock 2116 is shown engaged with the proximal threads 2204 and the insertion driver lock stop 2112 and insertion driver handle 2108 are also visible. The proximal end of distal anchor retention tube sub assembly 2300 is visible at the proximal end of dual anchor driver 2000.

Figure 13:
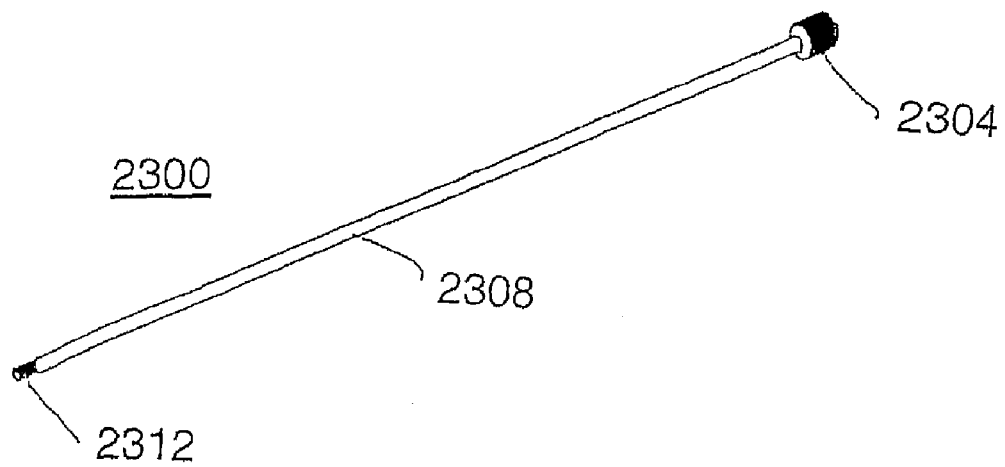
FIG. 13 is a perspective view of distal anchor retention tube assembly 2300.

FIG. 13 shows that the distal anchor retention tube sub assembly 2300 includes the cap 2304, threaded tube 2308 with distal threads 2312.

1504—Thread the distal threaded section 2216 of proximal anchor retainer 2200 (see FIG. 12) into the internal threads 416 in back of the proximal bone anchor 344 and place both onto dual-anchor driver 2000 so that the proximal bone anchor 344 is engaged with the proximal anchor driver section 2132 of the insertion driver shaft 2104.

1510—Engage insertion driver retainer lock 2116 onto the proximal threaded section 2204 of the proximal anchor retainer 2200 (see FIG. 11).

1516—Align distal bone anchor 340 onto the distal anchor driver section 2128 of the insertion driver shaft 2104.

1522—Rotate the cap 2304 of the distal anchor retention tube sub assembly 2300 to engage the distal threads 2312 with internal threaded section 368 of the distal bone anchor 340.

1528—Place dual anchor driver 2000 over the guide pin with extension. Deliver both anchors through the exchange cannula 704 using lateral fluoroscope for visualization.

1534—Adjust position of distal bone anchor 340 by driving both anchors until the proximal edge of the distal bone anchor 340 is close to flush with the distal endplate of the L5/S1 motion segment (the endplate on the proximal end of the L5 vertebra). As the distal endplate of the L5/S1 motion segment is unlikely to be perfectly perpendicular to the access channel 212, even when attempting for "flush" it is likely that one side of the distal bone anchor 340 will be closer to the intervertebral disc space 312 than the other, perhaps even protruding into the intervertebral disc space 312.

1540—Release distal bone anchor 340 from distal anchor retention tube sub assembly 2300 by rotating the cap 2304 and remove the distal anchor retention tube sub assembly 2300.

1546—Release insertion driver retainer lock 2116 on the dual anchor driver 2000 to free the insertion driver shaft assembly 2100 from the proximal anchor retainer 2200.

1552—Disengage dual anchor driver 2000 from distal bone anchor 340 and withdraw it from the proximal anchor retainer 2200.

C.2 Adjusting the Proximal Anchor Position

Figure 14:
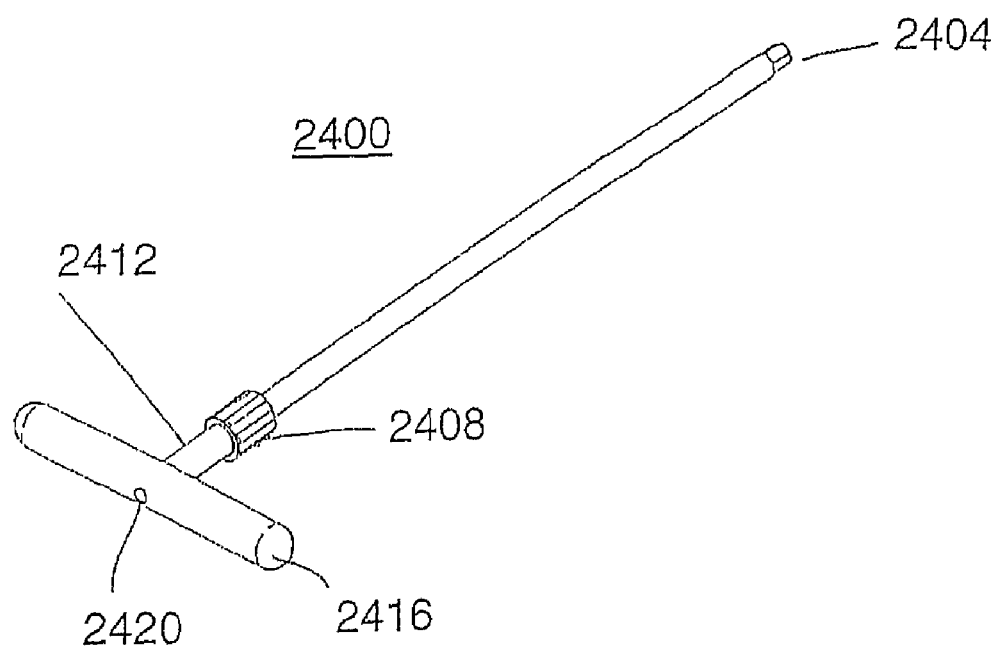
FIG. 14 is a perspective view of proximal anchor driver 2400.

FIG. 14 shows the proximal anchor driver 2400 with proximal anchor driver section 2404, retainer lock 2408, retainer lock stop 2412, handle 2416, and cavity 2420. The retainer lock 2408 has a set of internal threads (not shown) that engage the proximal threaded section 2204 of the proximal anchor retainer 2200 in much the same way as did the insertion driver retainer lock 2116 discussed above.

1558—Insert proximal anchor driver section 2404 of the proximal anchor driver 2400 into the proximal bone anchor 344 and attach to proximal anchor retainer 2200 with the internal threads in the retainer lock 2408. This proximal anchor driver 2400 only engages the proximal bone anchor 344 and thus cannot accidentally engage the distal bone anchor 340.

1564—Adjust position of proximal bone anchor 344 to advance the proximal bone anchor 344 to be flush with the S1 endplate. As noted above, "flush" in this context may have one side of the proximal bone anchor 344 protruding slightly into the intervertebral disc space 312 or conversely one side may be recessed slightly from flush. Optionally, the endplates may be processed adjacent to each inserted bone anchor with a radial cutter to remove any bone splinters created by the positioning of the bone anchors.

1570—Disengage the retainer lock 2408 of the proximal anchor driver 2400 from the proximal anchor retainer 2200 and remove the proximal anchor driver 2400 but leave proximal anchor retainer 2200.

1576—Remove guide pin with extension.

C.3 Insertion of Distal Plug

Figure 15:
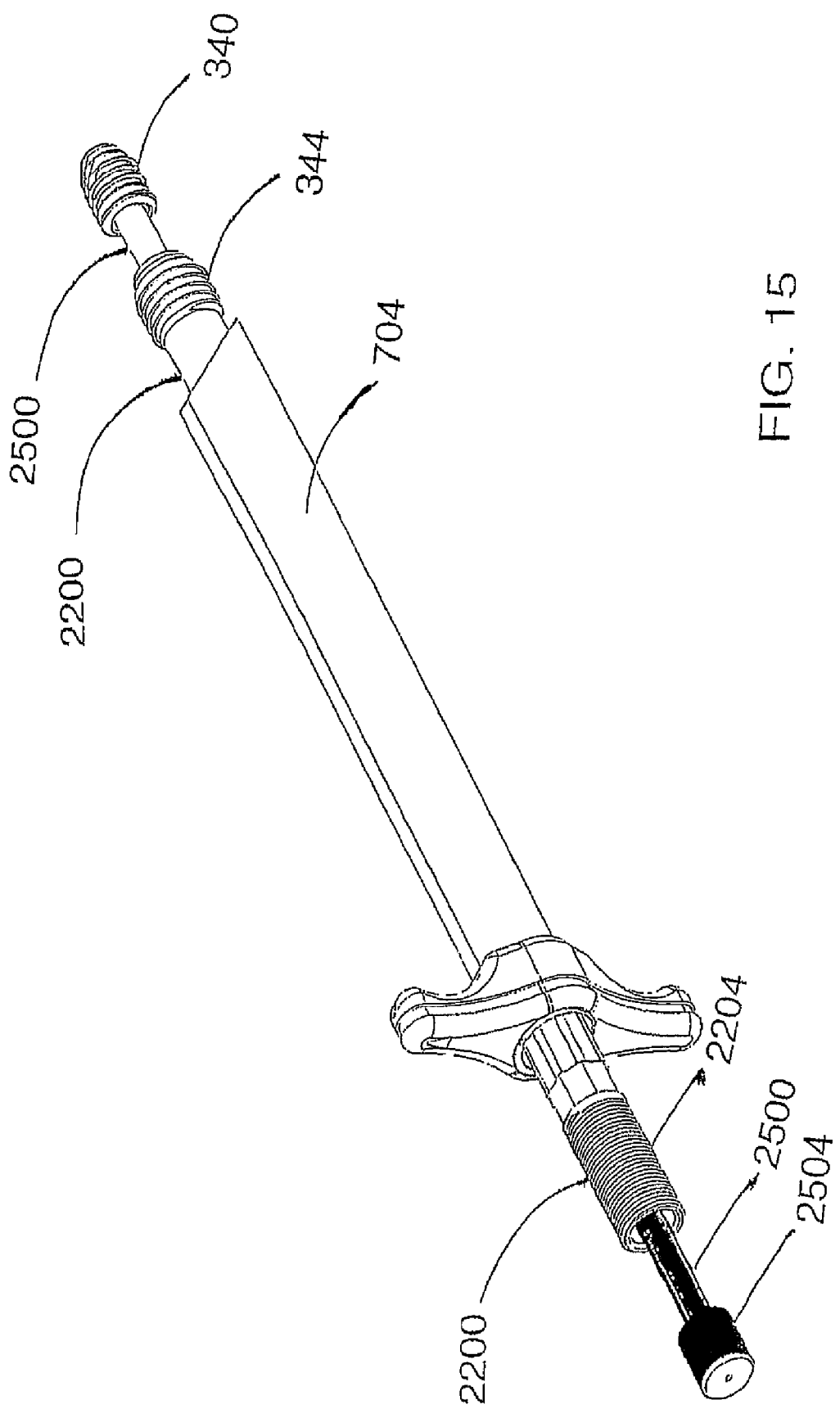
FIG. 15 is a perspective view of distal plug driver 2500 inserted in the proximal anchor retainer 2200 to insert the distal plug 380 (not visible here) into the distal bone anchor 340.

FIG. 15 shows the distal plug driver 2500 inserted in the proximal anchor retainer 2200 to insert the distal plug 380 (not visible here) into the distal bone anchor 340.

1582—Insert the threaded distal end of the distal plug driver 2500 into the cavity 398 of the distal plug 380 and engage the internal threads 396 inside the distal plug 380.

1588—Insert distal plug 380 using the distal plug driver 2500 through the proximal anchor retainer 2200, the proximal bone anchor 344, and into the distal bone anchor 340. Rotate the cap 2504 to engage external threads 384 on the distal plug 380 with the internal threads 368 of the distal bone anchor 340.

1592—Remove the distal plug driver 2500 from the proximal anchor retainer 2200.

C.4 Insertion of the Membranes and Distraction

Figure 16:
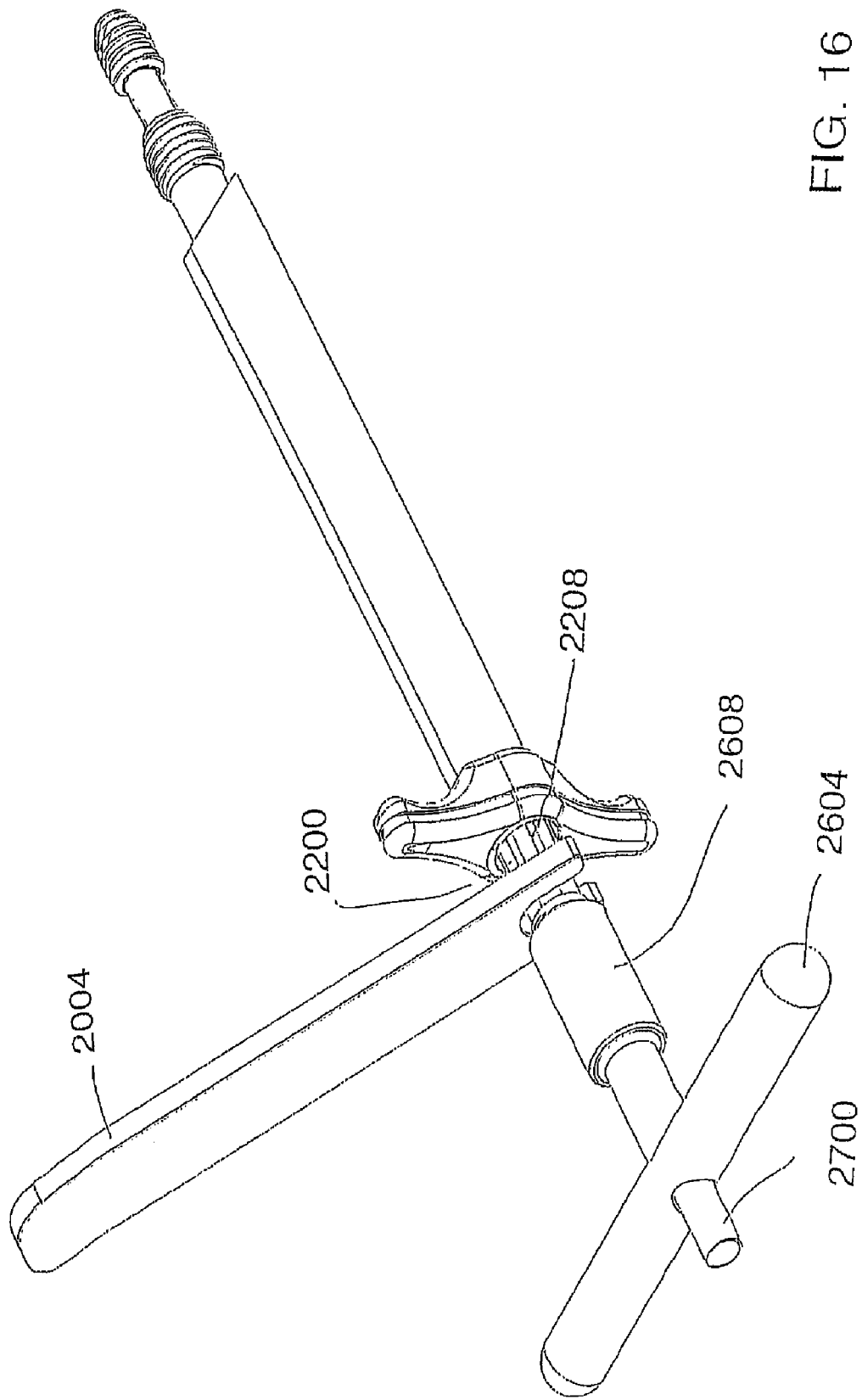
FIG. 16 is a perspective view of the distraction handle 2604 and the distraction lock 2608 engaged with the proximal end of the proximal anchor retainer 2200.

FIG. 16 shows the distraction handle 2604 and the distraction lock 2608 engaged with the proximal end of the proximal anchor retainer 2200. Partially visible is the proximal end of the membrane inserter assembly 2700. Retainer stabilizer 2004 may be used to engage the polygonal section 2208 to prevent rotation of the proximal anchor retainer 2200 while torque is being applied to other components.

Figure 17:
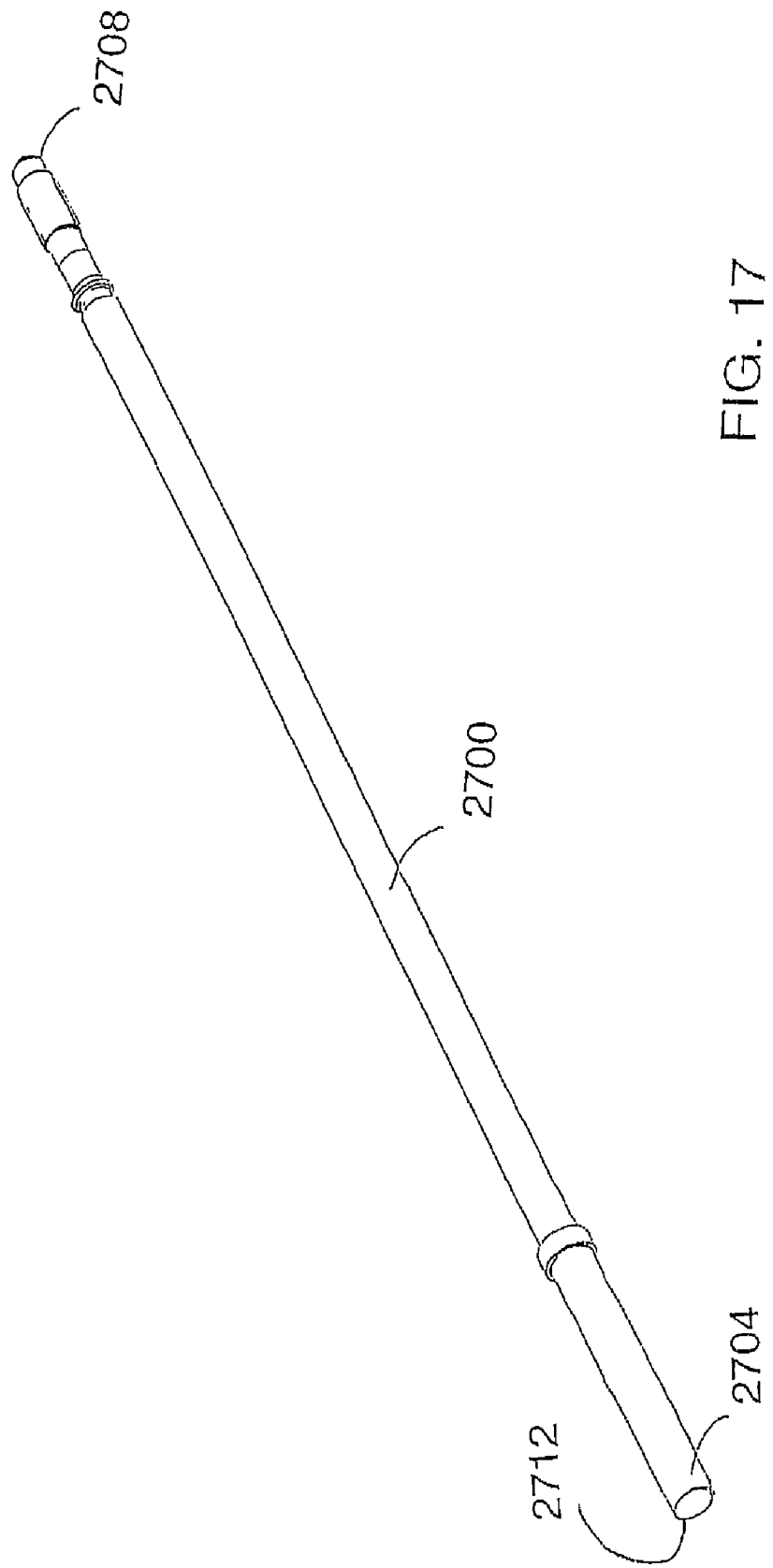
FIG. 17 is a perspective view of membrane inserter assembly 2700.

FIG. 17 shows membrane inserter assembly 2700 with proximal end 2704 and distal end 2708 and cannula 2712.

Figure 18:
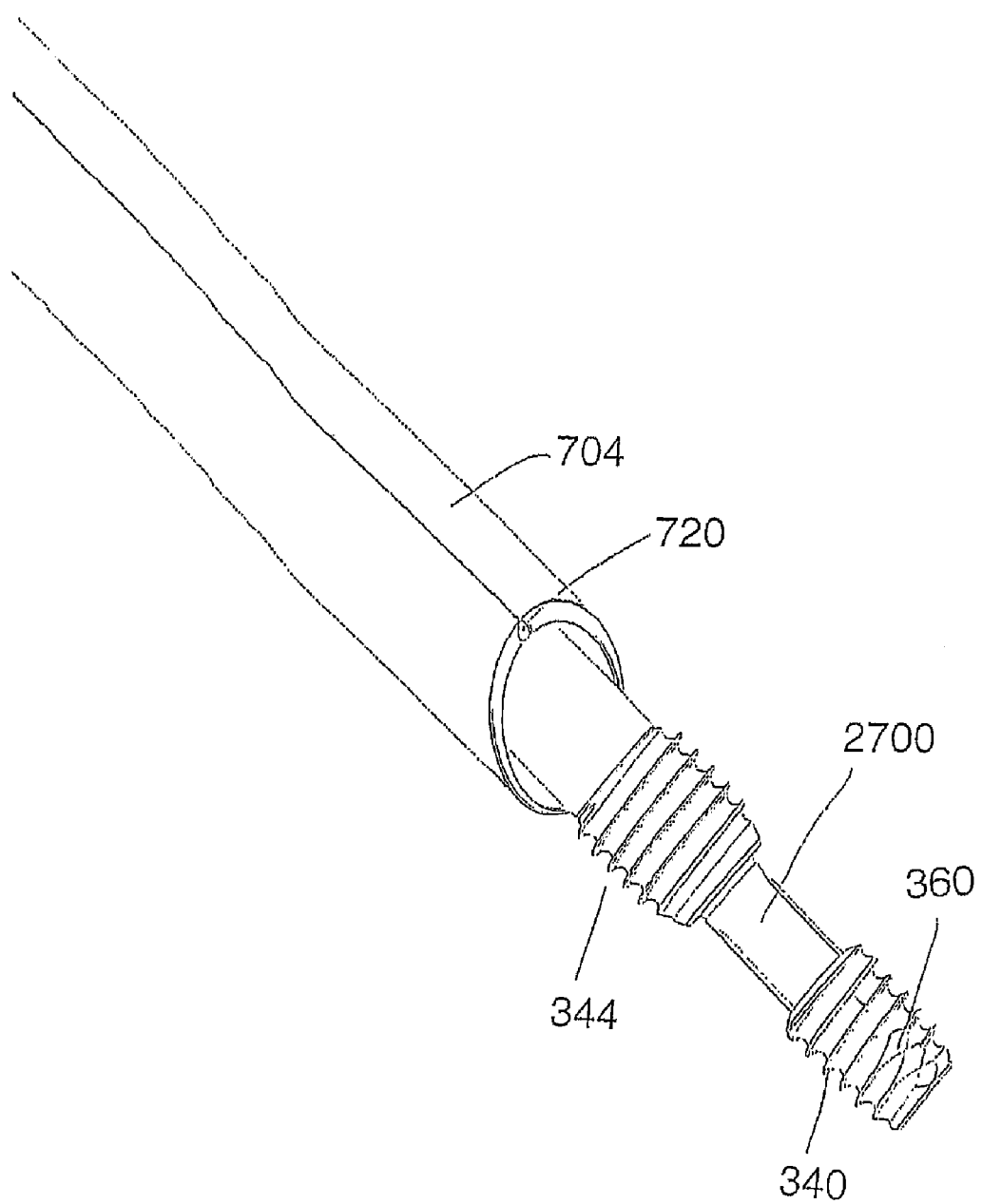
FIG. 18 is a perspective view of the distal portion of the membrane inserter assembly 2700.

FIG. 18 is a perspective view of the distal portion of the membrane inserter assembly 2700 with distal bone anchor 340 (with chip breaker 360); proximal bone anchor 344; and the distal end of exchange cannula 704 showing the channel 720 (without wire in this view).

Figure 19:
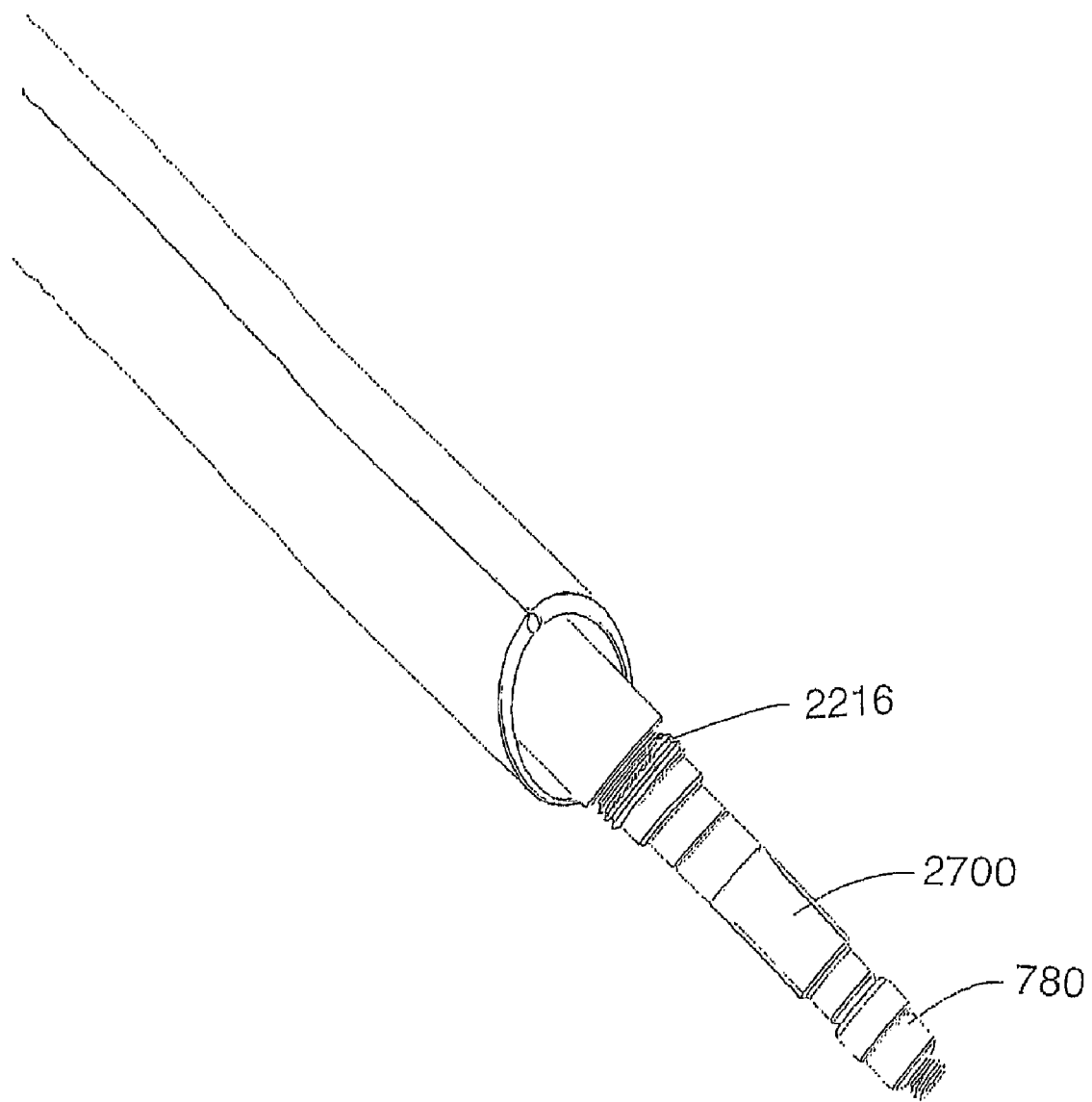
FIG. 19 is the view from FIG. 18 with the two bone anchors made invisible in order to make underlying components visible.

FIG. 19 is the view from FIG. 18 but removes the two bone anchors so that the distal plug 380 is visible along with the distal threaded section 2216 of the proximal anchor retainer 2200. Remove in this context is to render invisible so that the details that would not be visible are visible for purposes of illustration.

Figure 20:
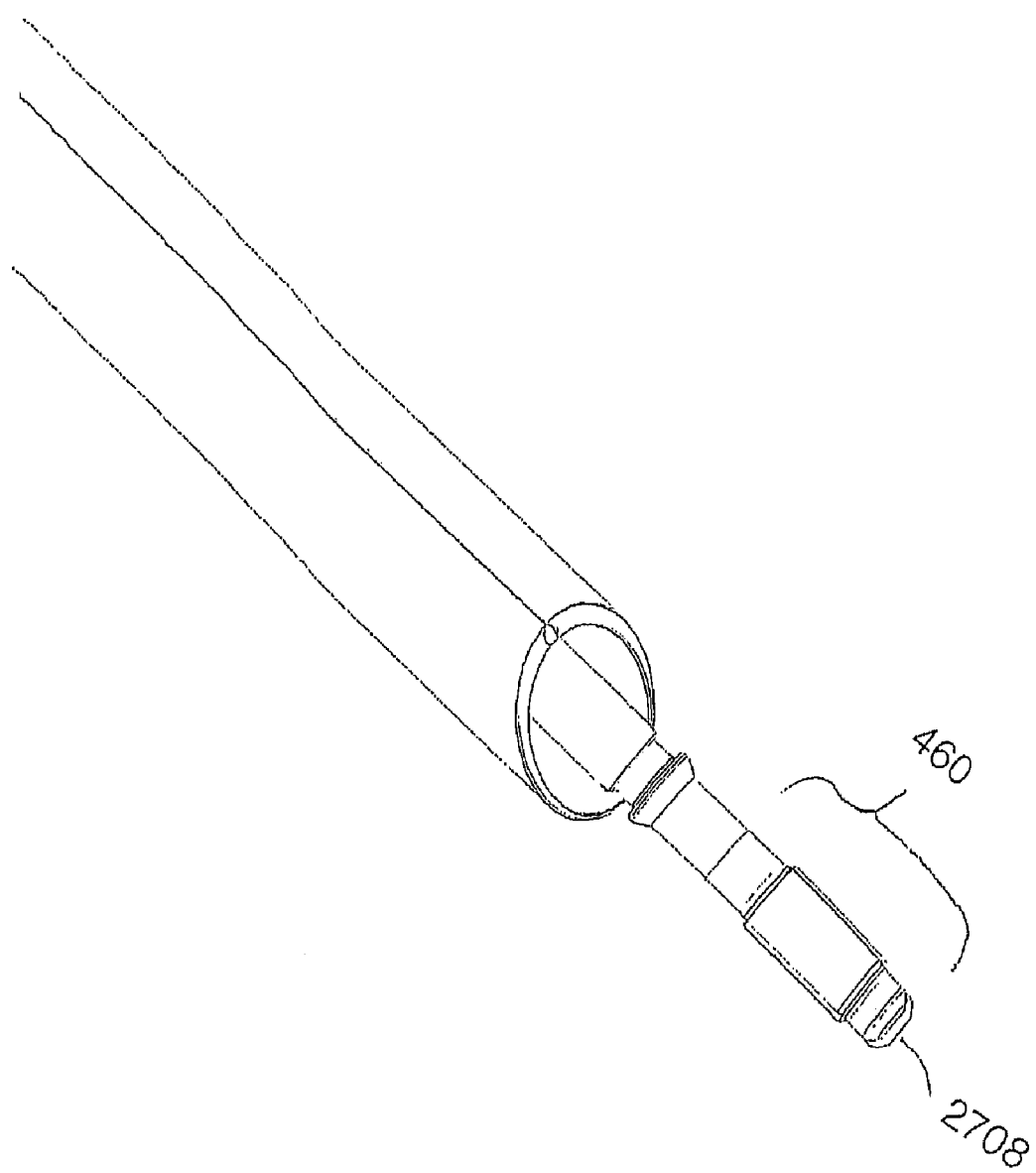
FIG. 20 alters the view from FIG. 19 by making the distal plug invisible and making the proximal anchor invisible to reveal details of the membrane inserter assembly 2700.

FIG. 20 removes the distal plug 380 and the proximal anchor retainer 2200 to reveal additional detail of the membrane inserter assembly 2700. Outermost membrane 460 covers the distal end 2708 of the membrane inserter assembly 2700.

Figure 21:
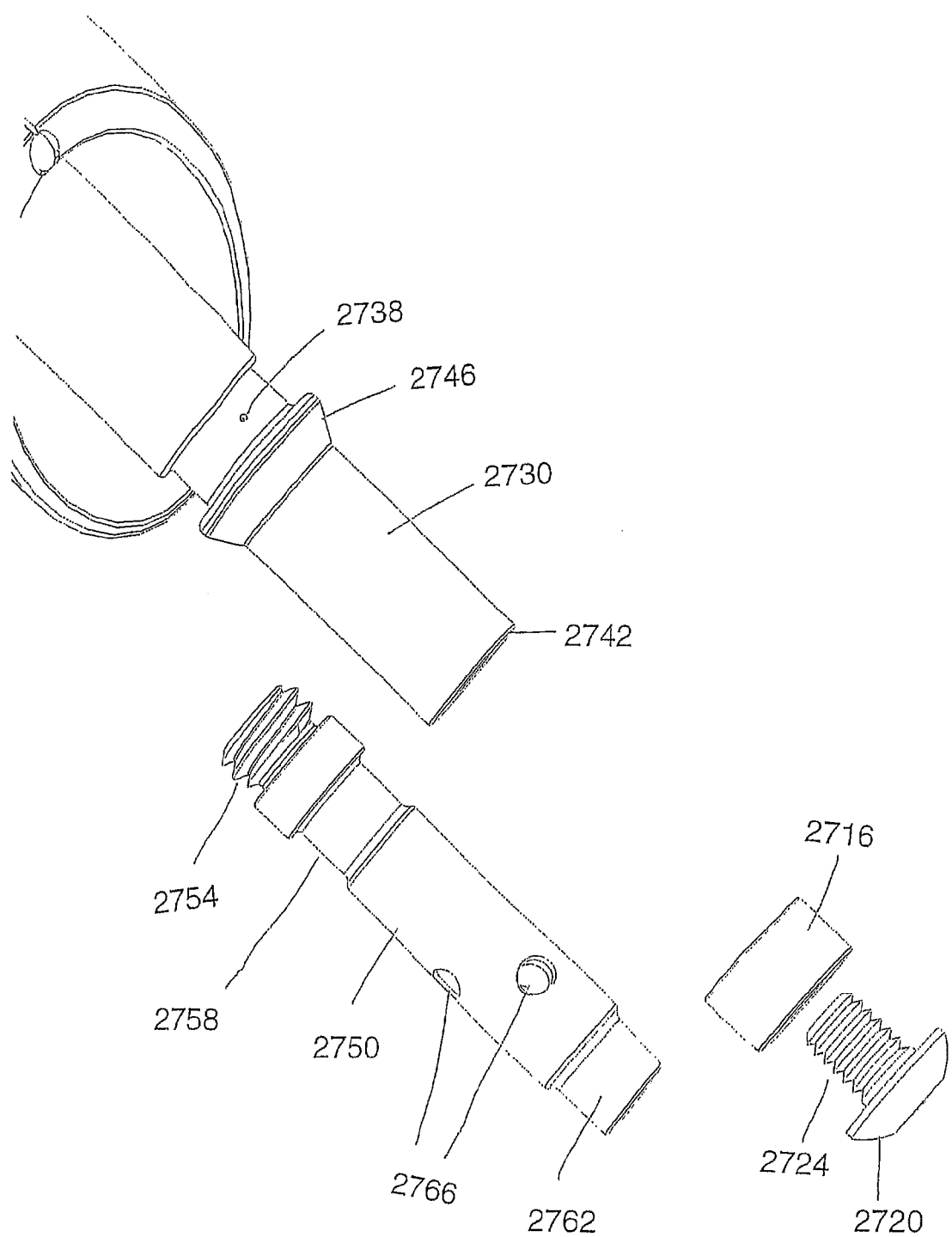
FIG. 21 alters the view from FIG. 20 by making the membranes invisible and separates the component to make details visible.

FIG. 21 removes the outermost membrane 460 and the innermost membrane 450. FIG. 21 also pulls apart the various components to make them individually visible. Thus, in FIG. 21, the button head cap screw 2720 is visible along with the threaded shank 2724. In FIG. 20, the threaded shank 2724 was engaged with a set of internal threads 2770 (see FIG. 22) of the distraction tip 2750 to hold a retainer ring 2716 and thus capture and retain the distal end of the innermost membrane 450 in the distal zone for the innermost membrane 2762. The path for the injection of prosthetic nucleus material includes a series of ports 2766 which are shown here perpendicular to the internal cannula but other orientations could be used. While a plurality of ports is shown on distraction tip 2750, a single port could be used.

Threaded proximal end 2754 of the distraction tip 2750 engages the internal threads 2734 (See FIG. 22) located away from the distal end of the distraction shaft adapter 2730 so that the proximal end of the innermost membrane 450 positioned in the proximal channel for the innermost membrane 2758 is held in an interference fit as the distal end 2742 of the distraction shaft adapter 2730 covers the proximal channel 2758. An air vent 2738 is positioned near the thread guard 2746 of the distraction shaft adapter 2730.

Figure 22:
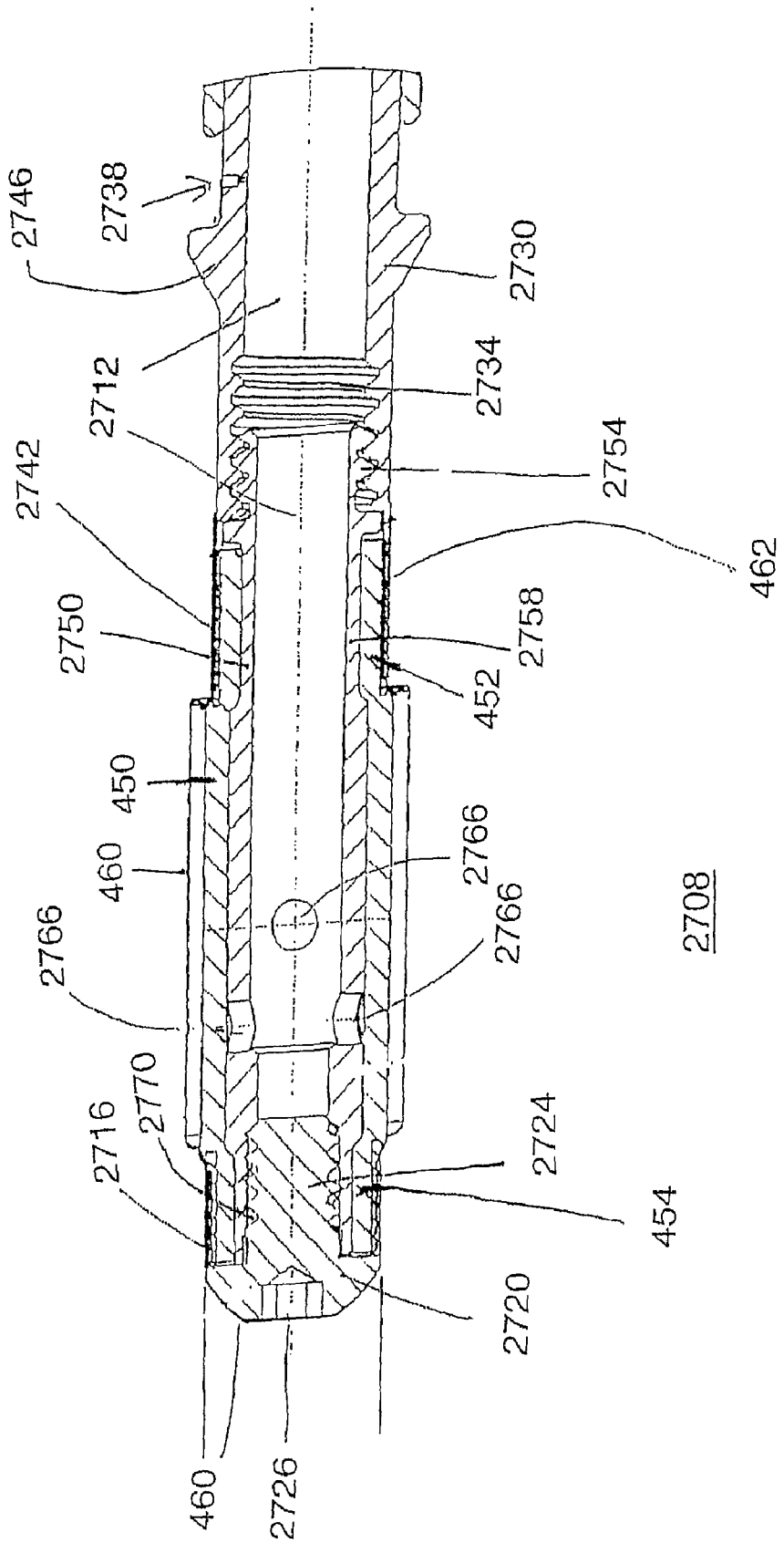
FIG. 22 is a cross section of the distal end 2708 of the membrane inserter assembly 2700.

FIG. 22 is a cross section of the distal end 2708 of the membrane inserter assembly 2700. The threaded button head cap screw 2720 is shown with threaded shank 2724 engaged with internal threads 2770 of distraction tip 2750. The threaded button head cap screw 2720 may be driven by a driver engaging an engagement section 2726. The button head cap screw 2720 is covered by the outermost membrane 460. The open distal end of the innermost membrane 450 is secured by the retainer ring 2716 held in place by the button head cap screw 2720. The open proximal end of the innermost membrane 450 is captured between the distraction tip 2750 at the proximal channel for the innermost membrane 2758 and the distal end 2742 of the distraction shaft adapter 2730 as the threaded proximal end 2754 of the distraction tip 2750 is tightened into the internal threads 2734 of the distraction shaft adapter 2730.

1598—Place membrane inserter assembly 2700 with membranes 450 and 460 through proximal anchor retainer 2200 and the proximal bone anchor 344 and into the distal bone anchor 340 to contact the distal plug 380. (Note that there is no assembly step for the membrane inserter assembly 2700 with set of membranes during the surgery as this is assembled and sterilized before shipping to the hospital ready to insert).

The membrane inserter assembly 2700 may include optional sheath to protect the outermost membrane 460. The sheath is forced back to expose the outermost membrane 460 when the membrane inserter assembly 2700 is advanced as the distal end of the sheath has a wider cross section than the rest of the sheath. When the distal end of the sheath hits a constriction within the proximal anchor retainer 2200 the sheath stops advancing and the membrane inserter assembly 2700 with the membranes continues to move distally and the membranes become unsheathed. Before the sheath is forced back by the constriction, the sheath is retained in the sheathed position by a friction fit with the outermost membrane 460.

1604—Place distraction handle 2604 and distraction lock 2608 over the membrane inserter assembly 2700 and engage onto the proximal threaded section 2204 of the proximal anchor retainer 2200. Rotation of the distraction handle 2604 will cause the threaded end of the distraction lock 2608 to advance distally and to push the membrane inserter assembly 2700 as the distraction handle 2604 and the distraction lock 2608 move along the proximal threaded section 2204 of the proximal anchor retainer 2200. As the membrane inserter assembly 2700 is in contact with the distal plug 380 which is engaged with the distal bone anchor 340 which is in turn engaged with the distal vertebral body 304, rotation of the distraction handle 2604 moves the distal vertebral body 304 relative to the proximal bone anchor 344 engaged with the proximal vertebral body 308 to increase the intervertebral disc space 312.

1610—Holding the proximal anchor retainer 2200 stationary (perhaps with retainer stabilizer 2004) turn the distraction handle 2604 to impose distraction. Depending on the threading used, this may impose approximately 2 millimeters of distraction per 360 degrees of rotation. A set of shoulders limit the travel of the of the proximal anchor retainer 2200 to a fixed maximum distraction which may be approximately 15 millimeters.

C.5 Injection of the Prosthetic Nucleus Material

Figure 23:
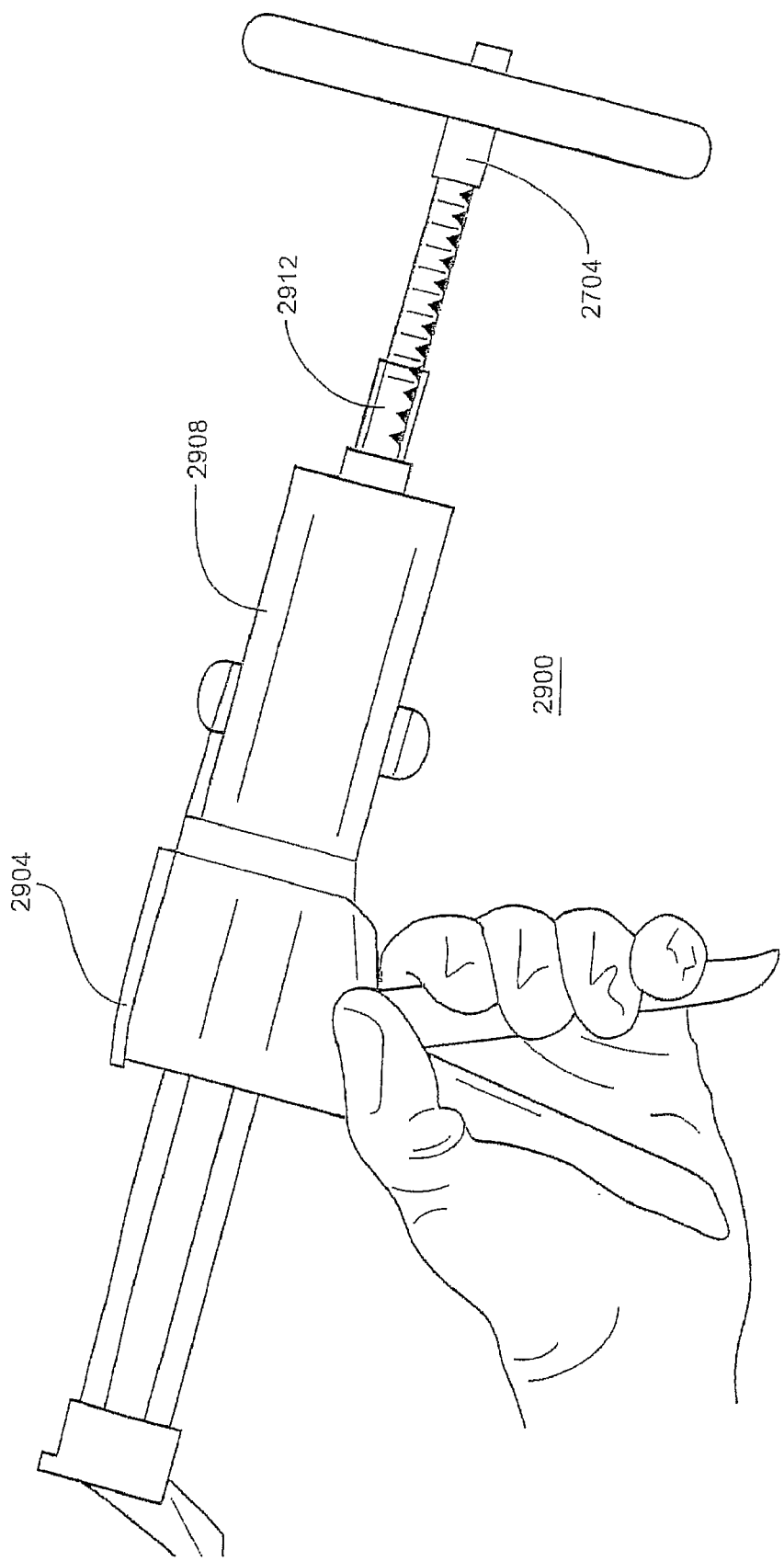
FIG. 23 is an illustration of the use of an injection dispenser assembly 2900 to inject prosthetic nucleus material.

FIG. 23 provides an illustration of an injection assembly 2900.

1616—Begin to assemble delivery tools for prosthetic nucleus material 464 by attaching dual chamber container 2908 to injection dispenser 2904. Remove the cap (not shown) from the dual chamber container 2908 and advance the plunger in the injection dispenser to dispense a small amount of material so as to purge air from the dual chamber container 2908.

1622—Thread static mixing tip 2912 to the proximal end 2704 of the membrane inserter assembly 2700. If the static mixing tip 2912 did not come with suitable external threads, the static mixing tip 2912 may be modified to add the external threads.

1628—Attach injection dispenser 2904 with dual chamber container 2908 to the static mixing tip 2912.

1634—Inject prosthetic nucleus material 464 under live fluoroscopic imaging as the injected material is opaque to fluoroscopy. (In this case the prosthetic nucleus material 464 is silicone.) Air in the channel between the proximal end 2704 of the membrane inserter assembly 2700 and the air vent 2738 (See FIG. 21) will be vented out. The small amount of air between the air vent 2738 and the set of one or more ports 2766 will likely be captured in the innermost membrane 450. The air will be compressed and does not impinge on the functionality of the prosthetic nucleus 348. Allow pressure of the injected prosthetic nucleus material 464 to expand the set of membranes within the cavity. Optionally, the process may use a pressure gage and fill innermost membrane 450 until injection pressure reaches a designated target pressure. Injection pressures in the range of about 50 to 200 pounds per square inch often 85 to 100 pounds per square inch (PSI) may be suitable for some applications.

1640—Allow prosthetic nucleus material 464 to chance to become non-flowable. The process that alters the prosthetic nucleus material 464 from flowable to non-flowable will be contingent on the type of prosthetic used.

1646—Disengage injection assembly 2900 for prosthetic nucleus material 464 from the internal threads 2734 at the proximal end 2704 of the membrane inserter assembly 2700.

1652—Remove distraction handle 2604 and the distraction lock 2608 from engagement with the proximal threaded section 2204 of the proximal anchor retainer 2200.

C.6 Removal of the Membrane Inserter Assembly

Figure 24:
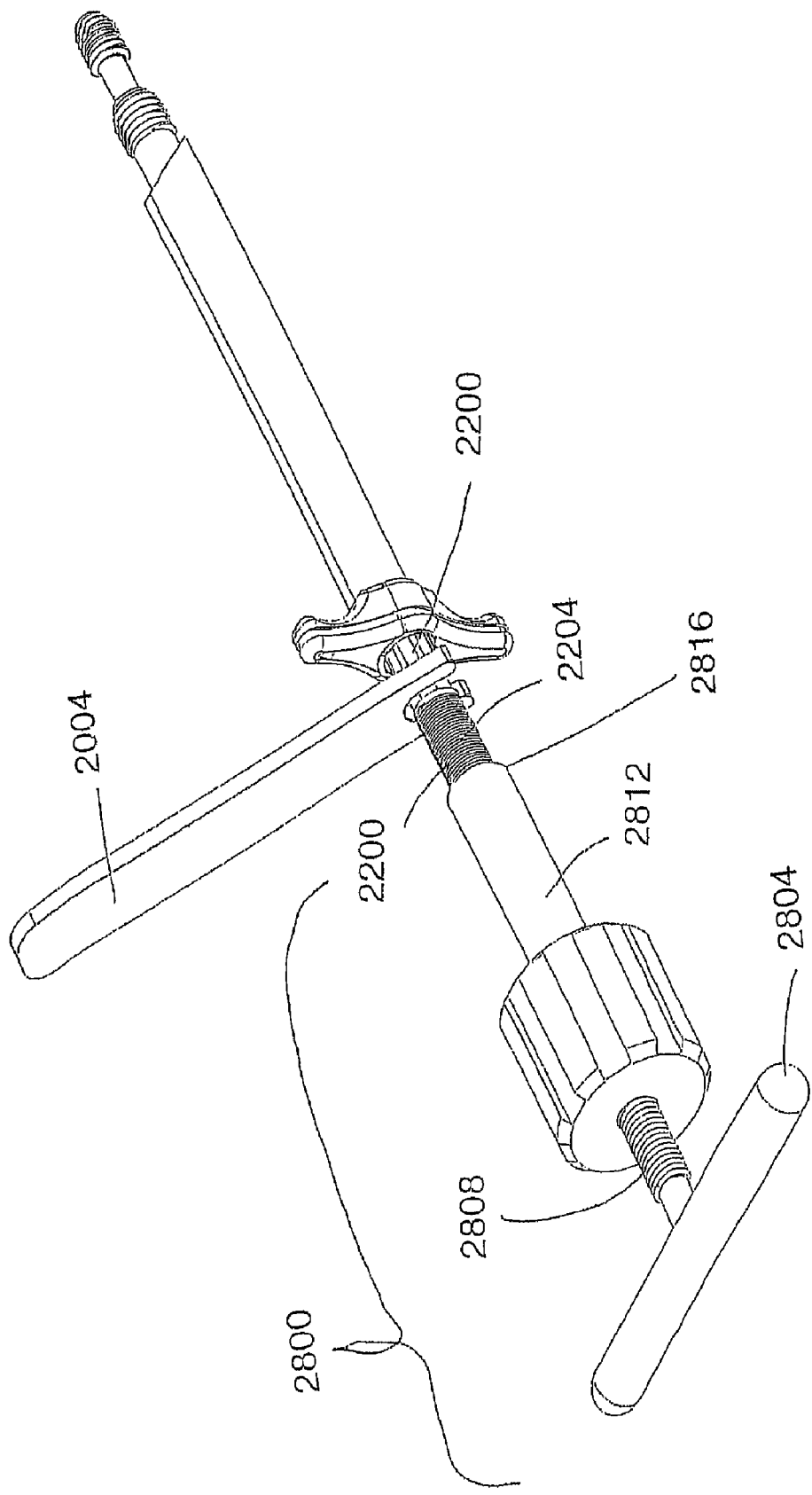
FIG. 24 is a perspective view of tube removal assembly 2800 connected to the other related components.

FIG. 24 shows the tube removal assembly 2800 with tube removal handle 2804 including the tube removal grip 2812 that pushes against the proximal end of the proximal anchor retainer 2200 while advancing the threaded tube removal shaft 2808 in the proximal direction to pull the membrane inserter assembly 2700 that is engaged with the tube removal shaft 2808 in the proximal direction.

1658—Engage the internal threads in the tube removal grip 2812 with the threads on the tube removal shaft 2808.

1664—Engage the external threads on the distal end of the tube removal shaft 2808 with the internal threads on the proximal end of the membrane inserter assembly 2700.

1670—Rotate the tube removal grip 2812 relative to threaded tube removal shaft 2808 of the tube removal assembly 2800 to move the distal end 2816 of the tube removal grip 2812 towards the proximal bone anchor 344. As the distal end 2816 of the tube removal grip 2812 makes contact with threaded proximal end 2204 of the proximal anchor retainer 2200, further rotation causes the distal end 2708 of the membrane inserter assembly 2700 to retract into the proximal bone anchor 344. Note a significant amount of force is necessary to break the silicone of the innermost membrane 450 at two places. Specifically, the open distal end of the innermost membrane 450 secured by the retainer ring 2716 held in place by the button head cap screw 2720 and the open proximal end of the innermost membrane 450 is captured between the distraction tip 2750 at the proximal channel for the innermost membrane 2758 and the distal end 2742 of the distraction shaft adapter 2730. Use of the screw threads to withdraw the membrane inserter assembly 2700 into the proximal bone anchor 344 causes a progressive, slow, and controlled withdrawal. It would be difficult to simply pull on the membrane inserter assembly 2700 and get this same level of control as substantial force is needed to rip or dislodge the innermost membrane 450 from the membrane inserter assembly 2700.

1676—Once the membrane inserter assembly 2700 is free of the innermost membrane 450, remove the membrane inserter assembly 2700 and the engaged tube removal assembly 2800.

C.7 Removal of the Proximal Anchor Retainer

No new figure is needed to visualize this operation as the relevant components and their interrelationships have been set forth above.

1682—Place proximal anchor driver section 2404 of the proximal anchor driver 2400 back through the proximal anchor retainer 2200 and engage the proximal bone anchor 344 with the hex tip to facilitate proximal anchor retainer 2200 removal.

1688—Holding the proximal bone anchor 344 stationary with the inserted proximal anchor driver 2400, turn proximal anchor retainer 2200 counter clockwise through use of the retainer stabilizer 2004 to unthread the proximal anchor retainer 2200 from the proximal bone anchor 344. Remove the proximal anchor retainer 2200 together with the proximal anchor driver 2400. This is done by simply grabbing the proximal ends of both as the proximal ends are both outside the body.

C.8 Insertion of the Proximal Plug.

Figure 25:
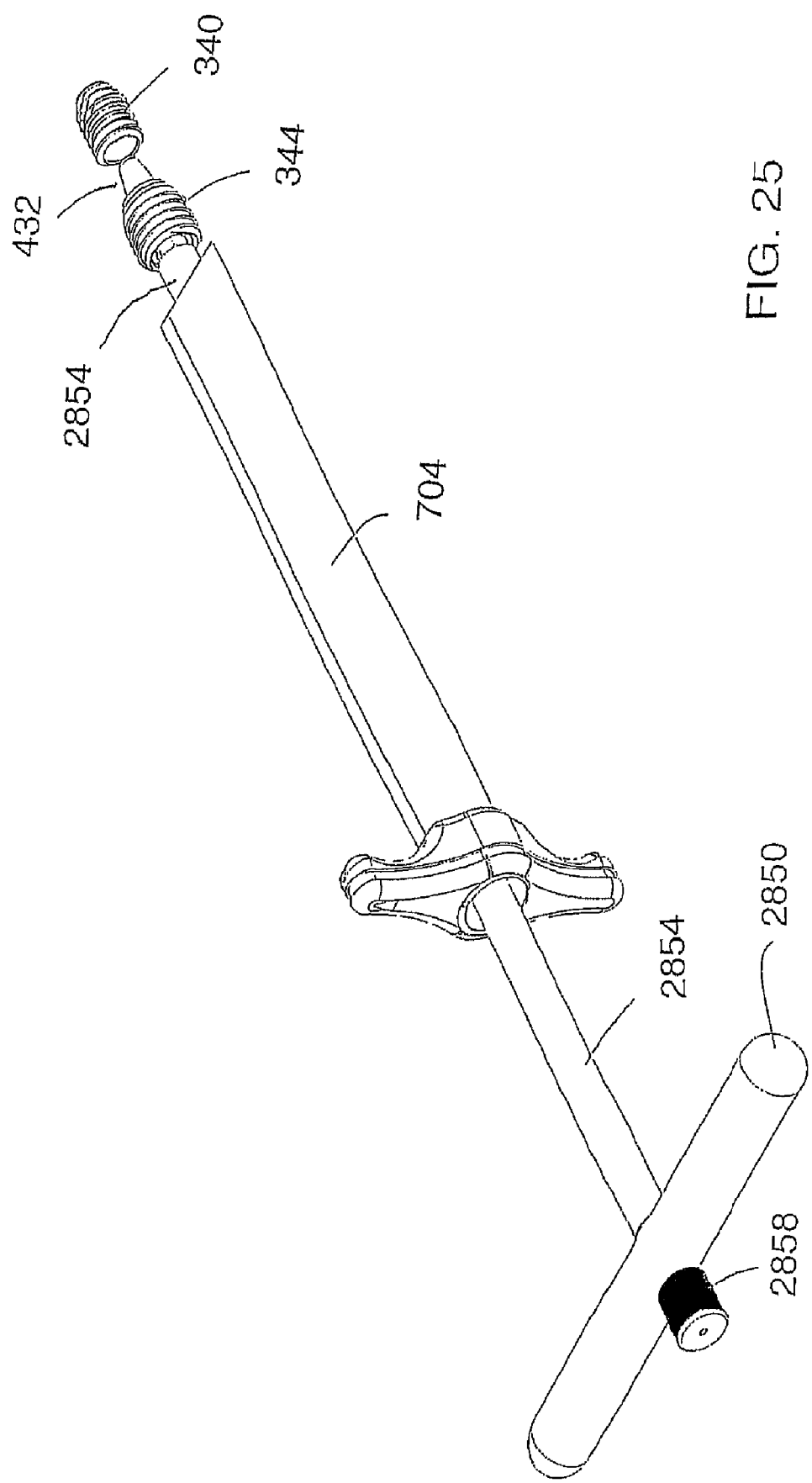
FIG. 25 is a perspective view of the two bone anchors 340 and 344 and the distal section 432 of proximal plug 420 in relation to relevant instrumentation items.

FIG. 25 is a perspective view of the two bone anchors 340 and 344 and the distal section 432 of proximal plug 420. The handle 2850, driver shaft 2854, and cap 2858 for retention tube (not visible here) are included in FIG. 25.

1694—Place the proximal plug 420 on the hex tip of the driver shaft 2854.

1700—Pass the distal end of the retention tube through the handle 2850 and driver shaft 2854 and thread into the internal threads 440 in the proximal end of the proximal plug 420 to secure the proximal plug 420 to the driver shaft 2854.

1706—Insert proximal plug 420 and the driver shaft 2854 through the exchange cannula 704 and into the proximal bone anchor 344 so that the distal section 432 of the proximal plug 420 makes contact with the previously injected prosthetic nucleus material 464 (not shown in FIG. 25). As the distal section 432 approaches the previously injected prosthetic nucleus material 464, it may first hit the proximal portion of the outermost membrane 460 or the proximal end of the innermost membrane 450 (if the proximal end of the innermost membrane 450 came loose from the membrane inserter assembly 2700 when the membrane inserter assembly 2700 was removed (rather than tearing)). The open proximal end 462 of the outermost membrane 460 or the silicone tube at the proximal end of the innermost membrane 450 will be pushed up and possibly inverted to go into the void 436 (See FIG. 3) in the injected prosthetic nucleus material (FIG. 3 element 464) as the distal section 432 of the proximal plug 420 is moved into the void 436. FIG. 3 shows the void 436 as roughly the same shape as the exterior of the distal section 432 of the proximal plug 420. This is an artifact of the model used to create the drawing. The actual shape of the void 436 is apt to be irregular as the void 436 is shaped based on the geometry of the membrane inserter assembly 2700 discussed above.

1712—While verifying that the proximal bone anchor 344 is not advancing (using the fluoroscope as the proximal anchor retainer 2200 has been removed and there is nothing beyond the resistance of the bone holding the proximal bone anchor 344 from rotating), torque the external threads 424 on the proximal plug 420 into the internal threads 416 on the proximal bone anchor 344.

1718—Continue threading the proximal plug 420 until the distal section 432 substantially fills the void 436 in the prosthetic nucleus material 464 within the innermost membrane 450.

1724—Turn the cap 2858 on the proximal plug retainer tube counter clock wise to release the proximal plug 420 from the driver shaft 2854 and remove the driver shaft 2854 from the exchange cannula 704.

1730—Verify completion of steps with fluoroscopy and remove exchange cannula 704 with fixation wire from access channel

1736—Close Access Channel 212.

Details on An Outermost Membrane

Figure 26:
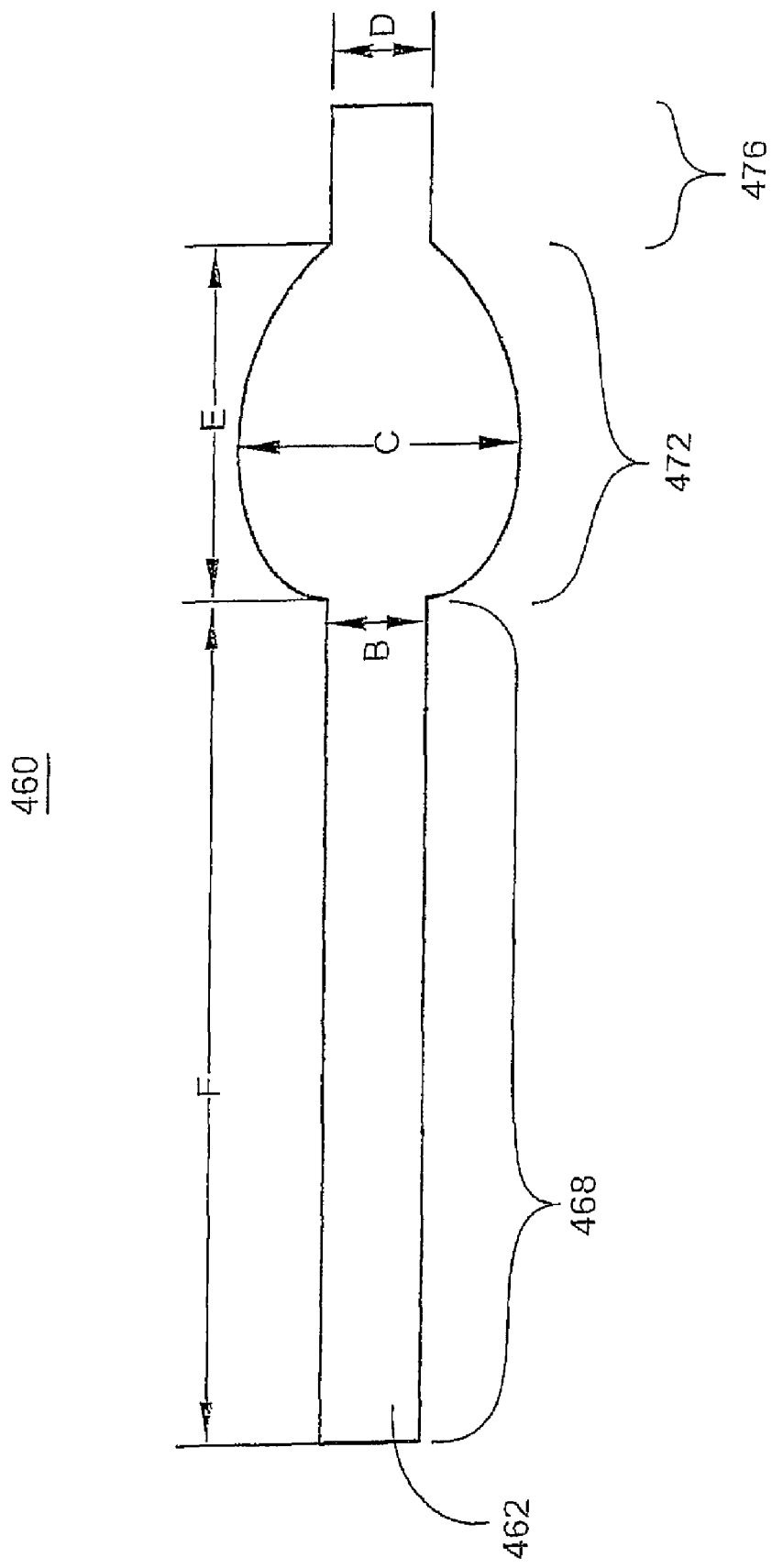
FIG. 26 is a profile of a woven membrane created for use as an outermost membrane 460.

FIG. 26 shows a profile of a woven membrane created for use as an outermost membrane 460. This woven membrane is created on a loom that can weave three-dimensional shapes so that the outermost membrane 460 is preformed into a desired configuration. A pair of biocompatible polyester yarns may be used. For example, yarns made of PET (polyethylene terephthalate) may be used. By way of example and not of limitation, an example of a two yarn combination that may be used is 1/20/18/0 PET BT (1 ply, 20 denier per ply, 18 filaments per ply, 0 twist in the raw material, Polyethylene Terephthalate, Bright surface) and 1/40/27/0 PET SD (1 ply, 40 denier per ply, 27 filaments per ply, 0 twist in the raw material, Polyethylene Terephthalate, Semi-dull surface).

The outermost membrane 460 may be thought of as three regions. The most proximal region is the inlet end 468 from the open proximal end 462 to the disc portion 472. The disc portion 472 is created to be substantially the shape of an expanded prosthetic nucleus 348 for a given application. Frequently, the disc portion 472 will be sized larger than the expected maximum size of the space created by removal of disc material. As the woven membrane in some implementations is intended to be a semi-compliant limit upon the highly compliant innermost membrane 450, the woven membrane is not adapted for a high degree of expansion of the surface area of the outermost membrane 460. The outermost membrane 460 increases in volume (primarily or exclusively) by having the material unfold or unfurl as the innermost membrane 450 expands with the inflation pressure of the injected prosthetic nucleus material 464. Woven material is often capable of some degree of expansion as fibers change orientation within the woven pattern but the woven material is unlikely to have a great capacity for deflection under load (either elastic or plastic elongation) unless the fibers can undergo elongation under the expected loading.

Figure 27:
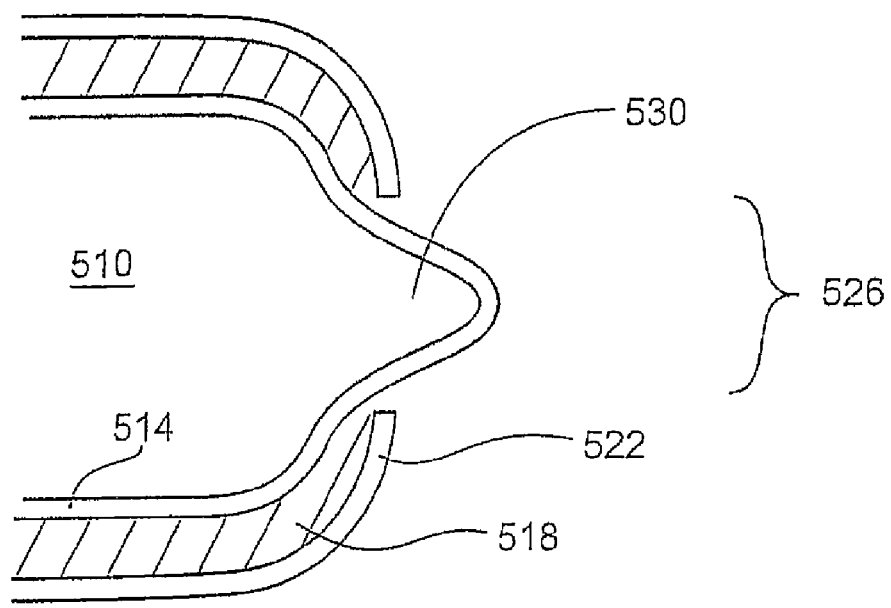
FIG. 27 is conceptual drawing to convey the problem associated with a prosthetic nucleus bounded only by a highly compliant membrane bulging out of an opening in an annulus fibrosus.
Figure 28:
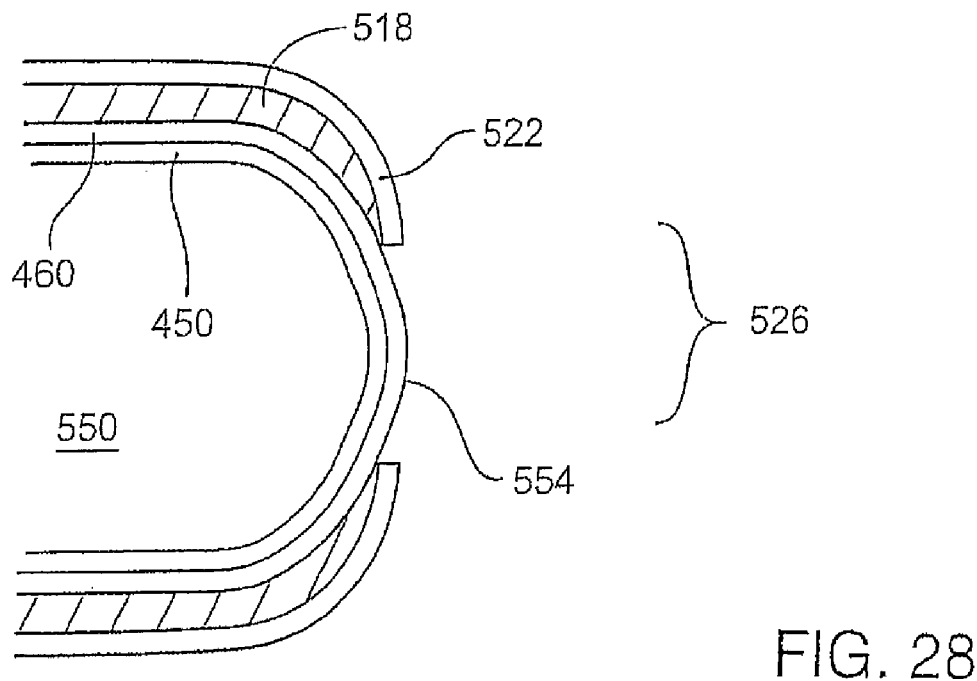
FIG. 28 is in contrast to FIG. 27 and illustrates the effect of having a semi-compliant membrane that limits the egress out of the same opening in the annulus fibrosus to a mild protrusion rather than a bulge.

The value of having a non-compliant outer membrane 460 is illustrated by the conceptual drawings FIG. 27 and FIG. 28. FIG. 27 shows a cross section of a portion of a prosthetic nucleus 510 using a single compliant membrane 514. The compliant membrane 514 complies to the shape of the residual nucleus pulposus 518 but bulges out in a prosthetic nucleus bulge 530 out a gap 526 in the annulus fibrosus 522. A prosthetic nucleus bulge 530 may have undesired consequences analogous to those resulting from a herniated disc.

In contrast, FIG. 28 shows a prosthetic nucleus 550 with a compliant innermost membrane 450 and a semi-compliant outermost membrane 460 which limits the compliancy of the innermost membrane 450 so that instead of a prosthetic nucleus bulge 530 from an unfettered compliant membrane, there is a mild protrusion 554 out of the gap 526 in the annulus fibrosus 522. It may be advantageous to have an outermost membrane 460 such as those described within this disclosure that limits the highly compliant innermost membrane 450 without impeding the transfer of loading to intervertebral disc structures during loading of the spinal motion segment.

By way of example, the woven fabric may have about 47 picks per inch. Again by way of example, the woven fabric may have a thickness on the order of magnitude of 0.005 inches thick. A set of dimensions is provided to give a sense of scale to FIG. 26. It is recognized that these dimensions may need to be adjusted depending on the anticipated size of the prosthetic nucleus 348 required. For examples, a larger patient may have a larger disc space than a diminutive patient and the disc spaces tend to get smaller in the more cephalad motion segments. The length of the inlet end 468 (dimension F) may be in the range of about 75 to 95 millimeters, often about 80 to 90 millimeters. The diameter (dimension B) may be in the range of 10 to 13 millimeters often about 11 to 12 millimeters.

The disc portion 472 may have a diameter (dimension C) of about 25 to 35 millimeters often about 27 to 30 millimeters and a length (dimension E) of about 30 to 45 millimeters, often about 35 to 40 millimeters. The diameter (dimension D) of the closed cap portion 476 may be in the range of about 12 to 15 millimeters and often in the range of about 13 to 14 millimeters and the length (dimension G) of the cap portion may in the range of 10 to 13 millimeters and often in the range of 11 to 12 millimeters.

Details on the Innermost Membrane

Innermost membrane 450, a highly compliant, highly expandable membrane, may be made of an elastomeric material, such as silicone rubber, such as that obtained from Nusil Silicone Technology located in Carpeneria, Calif., exhibiting a capacity for elongation of between about 500% and about 1500% and most preferably about 1000% and having a wall thickness of 0.035 inches. Other biocompatible materials may be used that have appropriate mechanical properties for use as an innermost membrane or an intermediate membrane (discussed below) with properties analogous to an innermost membrane.

D. Process of Loading Membranes

Figure 29:
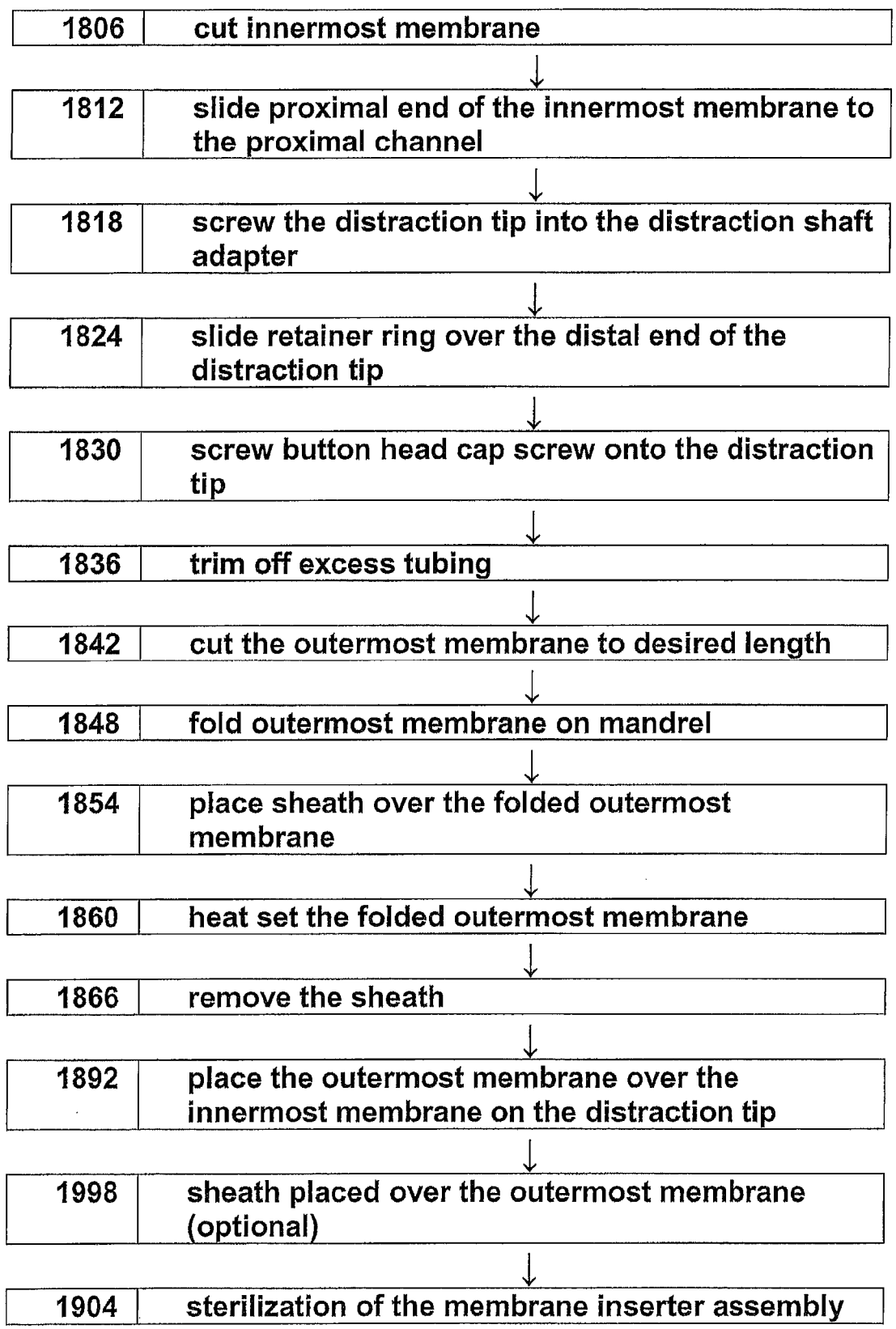
FIG. 29 is a flow chart for a process to load an innermost membrane and an outermost membrane to a membrane inserter assembly.

While the process will differ slightly if there is one or more intermediate membrane in addition to an outermost membrane 460 and an innermost membrane 450, it is useful to start with the more basic process 1800 of loading just an innermost membrane 450 and an outermost membrane 460. The process is summarized in FIG. 29. When reviewing these steps, it may be useful to refer to FIGS. 21 and 22.

1806—Starts with cutting a silicone tube made of the material to serve as the innermost membrane 450.

1812—Slide open proximal end 452 of the innermost membrane 450 distal end of the distraction tip 2750 to the proximal channel 2758.

1818—Screw the distraction tip 2750 into the distraction shaft adapter 2730 so that the threaded portion 2754 of the distraction tip 2750 engages the internal threads 2734.

1824—Slide retainer ring 2716 over the distal end of the distraction tip 2750 to the distal zone for the innermost membrane 2762.

1830—Screw button head cap screw 2720 onto the distraction tip 2750 to hold the retainer ring 2716 over the distal zone for the innermost membrane 2762 to capture what will become the distal end 454 of the innermost membrane 450. The button head cap screw 2720 serves as an atraumatic tip so that the contact from the button head cap screw 2720 on the distal plug 380 during the distraction of the intervertebral disc space 312 does not damage the outermost membrane 460.

1836—Trim off excess silicone tubing at edge of button head cap screw 2720.

1842—Cut the outermost membrane 460 from its delivered length to desired length. Laser cutting is one way of achieving suitable results.

1848—Fold outermost membrane 460 on mandrel As one of skill in the art will appreciate, the mandrel may be sized to emulate a distal end 2708 of the membrane inserter assembly 2700 with an innermost membrane 450 so that the outermost membrane 460 is folded to fit over an actual distal end 2708 of the membrane inserter assembly 2700 with an distal end 2708 of the membrane inserter assembly 2700.

Figure 30:
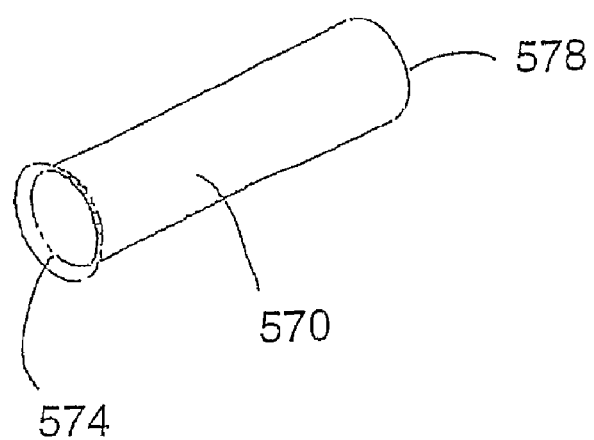
FIG. 30 is a perspective view of a sheath which may be used to protect the loaded set of membranes and may be used to help shape the folded outermost membrane.

1854—Place open proximal end 578 of sheath 570 (shown in perspective view in FIG. 30) over the folded outermost membrane 460 until it is covered by the sheath 570.

1860—Heat set the folds in the folded outermost membrane 460 in an oven. The time and temperature for the heat treatment are dependent on the specific material used for the outermost membrane 460.

1866—Remove the sheath 570.

1892—Place the open proximal end 462 of the outermost membrane 460 over the innermost membrane 450 previously loaded on the distraction tip 2750.

1998—Sheath 570 placed back over the outermost membrane 460.

1904—Sterilization of the membrane inserter assembly 2700 may be done by conventional methods after the membrane inserter assembly 2700 is completed.

Materials

The distal bone anchor 340, proximal bone anchor 344, distal plug 380, and in some instances the proximal portion of the proximal plug 420 may be made from a suitable biocompatible material with adequate mechanical properties. A titanium alloy such as Ti6A14V may be a suitable choice.

Alternatives and Variations

Delivery to Motion Segment other than L5/S1.

In order to provide concreteness to the disclosure provided above, a specific motion segment was discussed. In this instance it was the L5/S1 motion segment. While the dimensions of components may be slightly different when implanted in a different motion segment, nothing in the above disclosure should be interpreted as limiting the disclosure to therapeutic treatment of the L5/S1 motion segment. Other motion segments including by way of example and not limitation the L5/L4 motion segment and the L3/L4 motion segment may benefit from delivery of a spinal motion preservation assembly that uses one or more teachings from the present disclosure.

No Distraction

One of skill in the art could make a delivery tool that delivers sets of membranes as discussed within this disclosure without the capacity to perform using the membrane insertion tool distraction.

Figure 31:
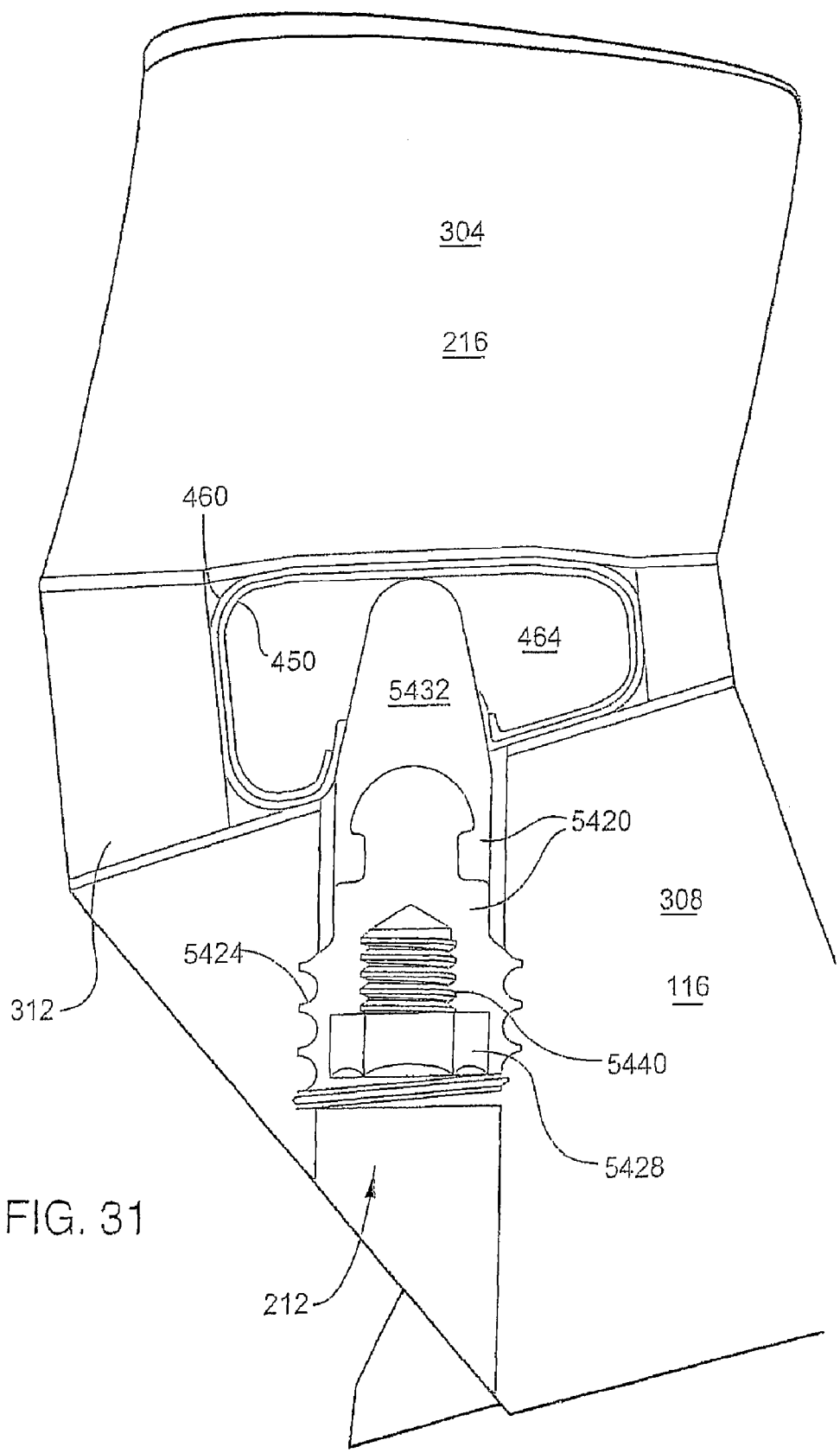
FIG. 31 is a cross section of a multi-membrane prosthetic nucleus in a spinal motion preservation assembly in a L5/S1 motion segment that does not include a proximal bone anchor or a distal bone anchor.

If the procedure will not include a distraction during the insertion of the membranes and before the insertion of the prosthetic nucleus material, then the procedure may not require the implantation of the distal bone anchor or the proximal bone anchor. FIG. 31 shows an illustration of this concept. Distal vertebra 304 (again L5 216) and proximal vertebra 308 (again S1 116) are separated by intervertebral disc space 312. The prosthetic nucleus material 464 has expanded innermost membrane 450 which is constrained by outermost membrane 460.

A proximal plug 5420 with set of external threads 5424 is implanted directly into the bone of the proximal vertebra 308 surrounding the access channel 212. Thus, the proximal plug 5420 may have a set of bone threads rather than machine threads to engage a set of internal threads in a proximal bone anchor 344. The delivery of the proximal plug 5420 made be done in an analogous way to the delivery of proximal plug 420 discussed above. Thus there is a set of internal threads 5440 and a driver engagement section 5428 to allow the distal section 5432 of the proximal plug 5420 to be driven into whatever void (not shown here) is left from the process of injecting the prosthetic nucleus material 464.

One Piece Proximal Plug

The plugs discussed above (420 and 5420) show a distal section (432 and 5432) that is placed over another component in the plug to form a plug assembly. This has the advantage of using a metal or analogous material for the driver section and the various threads while using a different material for the distal section. The distal section (432 and 5432) may be made of silicone or other material that has similar mechanical properties to the injected prosthetic nucleus material 464. (as noted above, the distal section is likely to be made from a stiffer material than the injected prosthetic nucleus material after it is non-flowable)

While this two material construction has its advantages, a plug could be created from just one material. Thus, the plug could be made entirely of metal or analogous material. This might be especially attractive if the void to be filled is relatively small so that there will be a substantial amount of prosthetic nucleus material surrounding the distal portion of the all metal plug.

Alternatively, the entire plug could be made of material with a substantial degree of elasticity, perhaps not as much as the injected prosthetic nucleus material 414, but with sufficient mechanical properties to withstand the direct application of torque and to engage internal threads in a proximal bone anchor 344. While there is an attraction to the use of plugs with external threads as threads lend themselves to reversible processes for subsequent removal of the proximal plug 420 if useful to provide additional therapy, the proximal plug 420 does not have to use a set of external threads. Other plug configurations such as plugs that use a snap insertion could be used.

Intermediate Membranes

While the examples provided above have used an innermost membrane 450 immediately adjacent to an outermost membrane 460, the present disclosure could be applied to a prosthetic nucleus with one or more intermediate membranes located between the innermost membrane 450 and the outermost membrane 460.

Thus, a prosthetic nucleus could use an innermost membrane 450, a highly compliant intermediate membrane, and an outermost membrane 460. This combination would have the two inner membranes expanded by the injection of the prosthetic nucleus material 464 and limited by the outermost membrane 460. One possible advantage of this combination would be the redundancy of two inner membranes that would react to the insertion of prosthetic nucleus material 464. Thus, if for whatever reason, one membrane was compromised so that it would not contain the prosthetic nucleus material 464 and would not expand as designed, the second inner membrane would expand. This concept could be extended to having two or more highly compliant intermediate membranes. The set of inner membranes and the delivery device could be adapted to engage the open ends of the inner membranes in the same place and in the same way. Alternatively, some inner membranes may be longer than others and engage different portions of the delivery device.

Another combination would be an innermost membrane 450 surrounded by a semi-compliant intermediate membrane or effectively two outer membranes. The innermost membrane 450 would expand under pressure from the injected prosthetic nucleus material 464 and would be limited in its expansion to prevent bulging by the two outer membranes. The pattern of fibers for the two outer membranes may optionally be oriented in different directions so that the mechanical properties of the two outer membranes in response to expansion pressure are not identical but compliment each other. This arrangement could assist the prosthetic nucleus in emulating the operation of the annulus fibrosus 254. This concept could be expanded to include more than one semi-compliant intermediate membranes.

One of skill in the art will appreciate that a prosthetic nucleus could be created having more than one compliant inner membrane and more than one semi-compliant outer membrane.

Absorbable Membranes

The set of membranes for the prosthetic nucleus provide boundaries for the injected flowable prosthetic nucleus material 464. Once this injected material has sufficiently changed to stop being flowable, there is less need for the membranes (especially in patients with an intact annulus fibrosus). Thus, the present disclosure can be extended to include the use of one or more membranes that are absorbable.

Other Materials for Outermost Membranes

In addition to the woven membrane described above, there are alternatives for the semi-compliant outer membrane 460 (sometimes referenced as a jacket or outer jacket). A braided structure may be used to limit bulging of the innermost membrane 450. The braided structure, like some woven fabrics, may be permeable with respect to the flowable state of the prosthetic nucleus material 464 but that is not a problem as the innermost membrane 450 is not permeable with respect to the prosthetic nucleus material 464. Another alternative would be to use a knitted material. In addition to woven, braided, or knitted, various nonwoven materials may be used. Nonwoven covers a range of materials made of fibers autogenously bonded through the action of a chemical agent or heating device, or adhering by means of resinous substances.

A film made of a biocompatible polymer such as PET may be used to provide a semi-compliant outermost membrane 460. The PET may be biaxially-oriented polyethylene terephthalate. The thickness of the PET film may be in the range of 0.0005 to 0.003 inches thick. Other processes and materials known to those of skill in the art may be made to perform semi-compliant membranes that are preformed into a desired configuration.

Coated Membrane

Another membrane for use in prosthetic nucleus devices is a coated membrane (or coated jacket). A foundation material for the coated membrane may be similar to the outermost membranes 460 described above (including membranes that would be permeable to the flowable prosthetic nucleus material such as some membranes made by weaving, braiding, knitting or a nonwoven process) can be made non-permeable to the flowable prosthetic nucleus material 464 by applying a coating to the membrane. This coating may be applied using one of a number of applications methods known in the art. These methods include coating, knife coating, spraying, dipping, casting, brushing, gravure or roll coating or other techniques known in the art.

The coating may be applied to the inner surface of the foundation material, the outer surface, or to both surfaces. Depending on the coating used and the foundation material, the coating is likely to become imbedded within the fibers rather than residing exclusively on a surface of the foundation material.

The coating would make the foundation material sufficiently non-permeable to the prosthetic nucleus material 464 to allow it to be used to contain the flowable material during creation of the prosthetic nucleus. The coating may also make the foundation material non-permeable to fluid and thus limit the ingress of fluid across the coated membrane in the deployed prosthetic nucleus implant. The coating may be selected based on the capacity for uniform adhesion to the foundation material and the ability to undergo the unfolding and any expansion expected in the coated membrane without cracking or otherwise compromising the barrier to the movement of the flowable prosthetic nucleus material 464. When using a foundation material made fibers of a particular polymer, it may be desirable to use a coating containing at least some of the same polymer to help promote interaction between the coating and the foundation layer.

Alternatively, a silicone, polyurethane, or other elastomer could be used as the coating material.

The mechanical properties of the membrane would provide the structural support to the prosthetic nucleus material 464 to make the prosthetic nucleus semi-compliant rather than highly compliant so that the prosthetic nucleus would not bulge out of openings in the annulus fibrosus 254 but would be limited to a mild protrusion.

A coated membrane may be thicker and more difficult to fold into a small configuration for delivery into the intervertebral disc space 312. Thus, the use of a coated membrane may be more attractive in procedures that are not placing a proximal bone anchor (such as element 344 in FIGS. 2-4) and thus do not limit the access to the intervertebral disc space 312 to a channel within the proximal bone anchor 344. If a proximal bone anchor 344 is not implanted into the axial bore, then the membrane insertion tool with the coated membrane may be close to the full diameter of the axial bore. Likewise a coated membrane may be an attractive option when delivering the coated membrane from a lateral access to the intervertebral disc space 312.

The coated membrane may be used as a single membrane or may be used as an outermost membrane in a series of membranes that includes an innermost membrane 450 that expands in response to the injection pressure of the injected prosthetic nucleus material 464.

Serial Delivery

While the present disclosure has focused on simultaneous delivery and deployment of the multiple membranes, one of skill in the art can appreciate that the membranes could be delivered serially. Serial delivery would start with the outermost membrane 460 and moving inward and finishing with the innermost membrane 450 and any highly compliant intermediate membranes that are to be expanded with the injected prosthetic nucleus material 464.

The outermost membrane 460 may be extended to its approximate final shape by the injection of a fluid or gas if the outermost membrane 460 is sufficiently non-permeable (as may be the case when using a film or a coated membrane). Alternatively, the outermost membrane 460 could be extended to its approximate final shape through the inflation of a balloon that is subsequently deflated and removed.

The outermost membrane 460 may be extended to its approximate final shape at the same time that one or more intermediate semi-compliant membranes are extended.

In some cases the outermost membrane 460 or a semi-compliant intermediate membrane may not need a specific process to partially expand the membrane as the delivery of the subsequent more inner membrane may be reliably initiated within the center of the earlier membrane and the expansion of the inner membrane works to expand the more outer membrane.

Lateral Delivery

The teachings of the present disclosure may be implemented by systems that do not rely exclusively on trans-sacral delivery routes. Thus, a multilayer membrane may be implanted using lateral access to the intervertebral disc space 312.

Alternative for Retaining

Membranes may be retained to the insertion tool using laser welded retaining rings that trap membrane material below the ring and in a channel formed for that purpose in the insertion tool. The innermost membrane 450 could be connected to the delivery tool by an adhesive or some other process known to skill in the art provided that the connection is suitable for use for a membrane to be placed under the intended insertion pressure.

Kits

For the convenience of the surgeons, collections of components for a procedure may be combined together in a kit. While it is possible that a kit would have all the components referenced above, in most instances, there is a distinction between re-usable components such as drills, dilators, and injection dispensers and the components that are either implanted in the body or used just for one procedure.

A kit may include, the single use components used to prepare the access channel including components described in more detail in the referenced applications and patent. These access channel preparation components may include the guide pin introducer, the guide pin handle, the stylet, the extension pin, and the dilator sheaths used for the drilling steps for the proximal and distal vertebral bodies.

The kit may also include the single use components for preparing the disc space. These components include a set of cutters to remove nucleus pulposus, preferably without undue abrasion to the endplates of the two adjacent vertebrae. The cutters may be of different throw lengths and may be set when deployed within the intervertebral disc space to have at different angles with respect to the access channel. There may be more than one cutter of a single type within the kit if that cutter type is expected to be used extensively. By way of example, the kit may have four different cutters although the kit could have less or more likely more than four cutters. The single use components for preparing the disc space may include a set of tissue extractors. For example, the kit might have a half dozen or so tissue extractors.

A prosthetic nucleus material kit might include the cartridge of the prosthetic nucleus material that fits within the injector dispenser and has an ample amount of the selected prosthetic nucleus material. The prosthetic nucleus material kit may include the static mixing tip. If the prosthetic nucleus material does not need a static mixing tip, then the tip of the cartridge may have external threads to engage the proximal end of the membrane inserter assembly 2700. The example given above used a dual cartridge, however, certain prosthetic nucleus material may require only one cartridge (and thus may not need a static mixing tip) or may more than two cartridges.

An implant components kit may include: a membrane inserter assembly 2700, preloaded with a set of two or more membranes. The membrane inserter assembly may include a sheath to protect the membranes. If the procedure will use a proximal bone anchor the kit may include the proximal bone anchor. The kit may include a proximal plug. However, in systems that use a variety of proximal plugs that differ in plug length to accommodate differences in intervertebral disc space thickness, the plugs may be provided independently of other kit components rather than providing several different proximal plugs of different lengths with a single kit.

If a distal bone anchor is to be used in the procedure, then the implant kit may include the distal bone anchor and the kit may include a distal plug. Some procedures may use a proximal bone anchor and a proximal plug without using a distal bone anchor and a distal plug.

Implant components kits may be specialized for certain sizes of motion segments. Thus a L5/S1 kit for a large patient may have larger proximal and distal bone anchors (longer) and use membranes adapted for a larger intervertebral disc space along with a longer proximal plug, than a L5/S1 kit for a patient with a smaller L5/S1 motion segment. Kits for more cephalad motion segments would be adjusted appropriately as these motion segments tend to be smaller than an L5/S1 motion segment.

If the procedure uses a single coated membrane rather than multiple membranes, then the membrane inserter would be adapted to deliver the single coated membrane and the implant kit would be adjusted accordingly.

If the procedure uses a series of membranes inserted serially, then there would be a series of membrane inserter assemblies rather than just one and the implant kit would be adjusted accordingly.

If the procedure did not use bone anchors, then the implant kit would be limited to the relevant membrane inserter assembly (or assemblies) and the proximal plug.

Thus, one can divide up the various items needed for a procedure into four specialized kits: single use access channel prep kit; single use disc space prep kit; prosthetic nucleus material kit; and implant components kit (with or without the proximal plug). Kits may be prepared that have combinations of the four specialized kits including a kit that combines four specialized kits.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

The legal limitations of the scope of the claimed invention are set forth in the allowed claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A prosthetic nucleus comprising:
a volume of cured prosthetic nucleus material at least partially confined by a membrane;
the membrane having a tool attachment section for attachment to a delivery tool to deliver the membrane to a target site via a delivery channel, the tool attachment section having a tool attachment section opening, the tool attachment section opening allowing prosthetic nucleus material before curing to flow through the tool attachment section to at least partially fill the membrane;
a portion of the membrane surrounding the tool attachment section opening having a cross sectional area that fits through the delivery channel;
the membrane having a second section in fluid communication with the tool attachment section opening that is at least partially filled with prosthetic nucleus material before curing without stretching the membrane so that a volume of cured prosthetic nucleus material at least partially confined by the membrane is too large to fit through the delivery channel but not large enough to stretch the membrane; and
the membrane having a second tool attachment section at a distal side of the second section, the second tool attachment section closed at a distal end of the membrane.

2. The prosthetic nucleus of claim 1 wherein the membrane is adapted for delivery via a trans-sacral delivery channel before at least partially filling with prosthetic nucleus material before curing to fill a void created by an at least partial nucleectomy.

3. The prosthetic nucleus of claim 1 wherein the membrane is adapted for use via a lateral approach to an intervertebral disc space before at least partially filling with prosthetic nucleus material to fill a void created by an at least partial nucleectomy.

4. The prosthetic nucleus of claim 1 wherein at least a portion of the prosthetic nucleus located in an intervertebral disc space is occupied by a distal end of a proximal plug inserted into a void in the cured prosthetic nucleus material.

5. The prosthetic nucleus of claim 1 wherein the membrane is coated with material to allow the membrane to retain flowable prosthetic nucleus material.

6. The prosthetic nucleus of claim 1 wherein the membrane is an outer membrane substantially enclosing an inner membrane whereby the outer membrane protects the inner membrane from damage and limits the inner membrane to prevent bulging from any gap in an annulus fibrosis that encircles an intervertebral disc space that receives the prosthetic nucleus.

7. A prosthetic nucleus comprising:
a volume of cured prosthetic nucleus material at least partially confined by a membrane;
the membrane having an inlet end which surrounds a portion of a delivery tool that delivers the membrane to a target site via a delivery channel, the inlet end having an opening at a proximal end of the membrane allowing prosthetic nucleus material to flow through the inlet end to at least partially fill the membrane before the prosthetic nucleus material cures to become non-flowable;
the inlet end of the membrane having an unfolded cross sectional area that fits through the delivery channel;
the membrane having a disc section in fluid communication with a distal end of the inlet end, the disc section that is at least partially filled with prosthetic nucleus material before curing without stretching the membrane so that a volume of cured prosthetic nucleus material at least partially confined by the membrane is too large to fit through the delivery channel but not large enough to stretch the membrane; and
a closed cap portion in fluid communication with a distal end of the disc section, the closed cap portion adapted to fit within a bore in an implanted bone anchor previously delivered through the delivery channel.

8. The prosthetic nucleus of claim 7 wherein the membrane is adapted for delivery via a trans-sacral delivery channel before at least partially filling with prosthetic nucleus material before curing to fill a void created by an at least partial nucleectomy.

9. The prosthetic nucleus of claim 7 wherein at least a portion of the prosthetic nucleus located in an intervertebral disc space is occupied by a distal end of a proximal plug inserted into a void in the cured prosthetic nucleus material.

10. The prosthetic nucleus of claim 7 wherein the membrane is coated with material to allow the membrane to retain flowable prosthetic nucleus material.

11. The prosthetic nucleus of claim 7 wherein the membrane is an outer membrane substantially enclosing an inner membrane whereby the outer membrane protects the inner membrane from damage and limits the inner membrane to prevent bulging from any gap in an annulus fibrosis that encircles an intervertebral disc space receiving the prosthetic nucleus.

* * * * *